United States Patent
Fram

(10) Patent No.: US 10,120,451 B1
(45) Date of Patent: Nov. 6, 2018

(54) SYSTEMS AND USER INTERFACES FOR DYNAMIC INTERACTION WITH TWO- AND THREE-DIMENSIONAL MEDICAL IMAGE DATA USING SPATIAL POSITIONING OF MOBILE DEVICES

(71) Applicant: DR Systems, Inc., San Diego, CA (US)

(72) Inventor: Evan K. Fram, Paradise Valley, AZ (US)

(73) Assignee: D.R. Systems, Inc., San Diego, CA (US)

( * ) Notice: Subject to any disclaimer, the term of this patent is extended or adjusted under 35 U.S.C. 154(b) by 179 days.

(21) Appl. No.: 14/593,330

(22) Filed: Jan. 9, 2015

Related U.S. Application Data

(60) Provisional application No. 61/947,621, filed on Mar. 4, 2014, provisional application No. 61/925,556, filed on Jan. 9, 2014.

(51) Int. Cl.
*G06F 3/044* (2006.01)
*G06F 3/01* (2006.01)
(Continued)

(52) U.S. Cl.
CPC ............ *G06F 3/017* (2013.01); *G06F 3/0484* (2013.01); *G06T 7/0012* (2013.01)

(58) Field of Classification Search
CPC .......... G06F 3/012; G06F 3/013; G06F 3/014; G06F 3/016; G06F 3/017; G06F 3/0346; G06F 2200/1637; G06F 3/03547; G06F 3/041; G06F 3/0412; G06F 3/0414; G06F 3/046; G06F 3/047; G06F 2203/041;
(Continued)

(56) References Cited

U.S. PATENT DOCUMENTS 6,151,023 A   11/2000  Chari
8,010,997 B2   8/2011  Limont et al.
(Continued)

OTHER PUBLICATIONS

Office Action dated Feb. 16, 2016 in U.S. Appl. No. 14/509,721.
(Continued)

*Primary Examiner* — Lun-Yi Lao
*Assistant Examiner* — Jarurat Suteerawongsa
(74) *Attorney, Agent, or Firm* — Michael Best & Friedrich LLP

(57) ABSTRACT

Embodiments of the present disclosure relate to systems and techniques for accessing data stores of medical images and displaying the medical images in substantially real-time to provide information in an interactive user interface. Systems are disclosed that may advantageously provide highly efficient, intuitive, and rapid dynamic interaction with two- and three-dimensional medical image data using spatial positioning of mobile devices. The systems may include interactive user interfaces that are dynamically updated to provide a virtual viewbox or window to two- and/or three-dimensional image data. A user may use the systems described herein to more quickly, thoroughly, and efficiently interact with image data including two-dimensional images, three-dimensional image data, and/or series of image data, as compared to previous systems. The systems described may also enable a user to efficiently view and interact with such image data using a small display, such as the display of a smartphone or tablet.

34 Claims, 25 Drawing Sheets

(51) Int. Cl.
*G06T 7/00* (2017.01)
*G06F 3/0484* (2013.01)

(58) Field of Classification Search
CPC .............. G06F 3/044; G06F 3/045; G06F 2203/04107; G06F 2203/04111; G06F 2203/04112; G06F 2203/04113; G06F 3/042; G06F 3/0421; G06F 3/0423; G06F 3/0428; G06F 2203/04109; G06F 3/1423; G06F 1/163; G06F 1/1647; G06F 1/1694; G09G 1/005; G09G 2330/021; G09G 2330/022; G09G 2330/023; G09G 2330/024; G09G 2330/025; G09G 2330/026; G09G 2330/027; G09G 5/14; G09G 5/373; G09G 2320/08; G09G 2354/00; G09G 2358/00; G09G 2370/22
See application file for complete search history.

(56) References Cited

U.S. PATENT DOCUMENTS

| | | | |
|---|---|---|---|
| 8,606,656 | B1 | 12/2013 | Franklin et al. |
| 8,954,884 | B1 | 2/2015 | Barger |
| 9,536,106 | B2 | 1/2017 | Fram et al. |
| 9,916,435 | B2 | 3/2018 | Fram |
| 2002/0147717 | A1 | 10/2002 | Barros |
| 2003/0055686 | A1 | 3/2003 | Satoh |
| 2003/0184585 | A1 | 10/2003 | Lin et al. |
| 2005/0114788 | A1 | 5/2005 | Fabritius |
| 2005/0228874 | A1 | 10/2005 | Edged et al. |
| 2006/0017692 | A1 | 1/2006 | Wehrenberg |
| 2006/0223556 | A1 | 10/2006 | Xu |
| 2006/0236373 | A1 | 10/2006 | Graves et al. |
| 2006/0288095 | A1 | 12/2006 | Torok et al. |
| 2007/0006289 | A1 | 1/2007 | Limont et al. |
| 2007/0143851 | A1 | 6/2007 | Nicodemus et al. |
| 2007/0282631 | A1 | 12/2007 | D'Ambrosia |
| 2008/0094368 | A1 | 4/2008 | Ording |
| 2009/0138800 | A1 | 5/2009 | Anderson |
| 2009/0222914 | A1 | 9/2009 | Ozawa |
| 2010/0017874 | A1 | 1/2010 | Piccinini et al. |
| 2010/0131294 | A1 | 5/2010 | Venon |
| 2010/0199197 | A1 | 8/2010 | Faletski et al. |
| 2010/0240996 | A1* | 9/2010 | Ionasec ............... G06T 7/0016 600/443 |
| 2010/0271177 | A1 | 10/2010 | Pang |
| 2010/0313239 | A1 | 12/2010 | Chakra et al. |
| 2011/0122155 | A1 | 5/2011 | Zechlin |
| 2011/0191343 | A1 | 8/2011 | Heaton et al. |
| 2012/0133601 | A1 | 5/2012 | Marshall |
| 2012/0154431 | A1* | 6/2012 | Fram ................... G06F 3/0338 345/619 |
| 2012/0183173 | A1 | 7/2012 | Li et al. |
| 2012/0190301 | A1 | 7/2012 | Hart |
| 2012/0233670 | A1 | 9/2012 | Bonnes et al. |
| 2012/0239950 | A1 | 9/2012 | Davis et al. |
| 2012/0253845 | A1 | 10/2012 | Bocirnea |
| 2012/0254981 | A1 | 10/2012 | Levien et al. |
| 2012/0297490 | A1 | 11/2012 | Barraclough et al. |
| 2012/0323607 | A1 | 12/2012 | Jin et al. |
| 2013/0141366 | A1 | 6/2013 | Ritter |
| 2013/0218583 | A1 | 8/2013 | Marcolongo et al. |
| 2013/0218917 | A1 | 8/2013 | Bell |
| 2013/0253291 | A1 | 9/2013 | Dixon et al. |
| 2013/0316682 | A1 | 11/2013 | Vieira |
| 2013/0347055 | A1 | 12/2013 | Motoyama |
| 2014/0075502 | A1 | 3/2014 | Aissi et al. |
| 2014/0078694 | A1* | 3/2014 | Wissmar ............... G04G 17/04 361/749 |
| 2014/0100955 | A1 | 4/2014 | Osotio |
| 2014/0135036 | A1 | 5/2014 | Bonanni |
| 2014/0282943 | A1 | 9/2014 | Nikankin |
| 2014/0324469 | A1 | 10/2014 | Reiner |
| 2014/0343962 | A1 | 11/2014 | Xu |
| 2015/0101066 | A1 | 4/2015 | Fram |
| 2017/0068813 | A1 | 3/2017 | Fram |

OTHER PUBLICATIONS

Interview Summary dated Apr. 26, 2016 in U.S. Appl. No. 14/509,721.
Final Office Action dated Jun. 21, 2016 in U.S. Appl. No. 14/509,721.
Final Office Action dated Aug. 2, 2016 in U.S. Appl. No. 14/509,721.
Notice of Allowance dated Sep. 27, 2016 in U.S. Appl. No. 14/509,721.
U.S. Appl. No. 14/509,721, filed Oct. 8, 2014, Evan K. Fram.
U.S. Appl. No. 14/593,228, filed Jan. 9, 2015, Evan K. Fram.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
AGFA HealthCare, color brochure "IMPAX 6: Digital Image and Information Management," ©2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. ©2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologjes.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

(56) References Cited

OTHER PUBLICATIONS

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.

(56) References Cited

OTHER PUBLICATIONS

Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Office Action dated Oct. 16, 2017 in U.S. Appl. No. 14/593,228.
Office Action dated Jul. 31, 2017 in U.S. Appl. No. 15/356,082.
Interview Summary dated Nov. 3, 2017 in U.S. Appl. No. 15/356,082.
Notice of Allowance from the U.S. Patent and Trademark Office for U.S. Appl. No. 15/356,082 dated Jan. 10, 2018; (17 pages).
Examiner-Initiated Interview Summary from the U.S. Patent and Trademark Office for U.S. Appl. No. 15/356,082 dated Jan. 10, 2018 (1 page).
Examiner-Initiated Interview Summary from the U.S. Patent and Trademark Office for U.S. Appl. No. 14/509,721 dated Aug. 2, 2016 (1 page).
Final Office Action from the U.S. Patent and Trademark Office for U.S. Appl. No. 14/593,228 dated Jun. 20, 2018 (37 pages).

\* cited by examiner

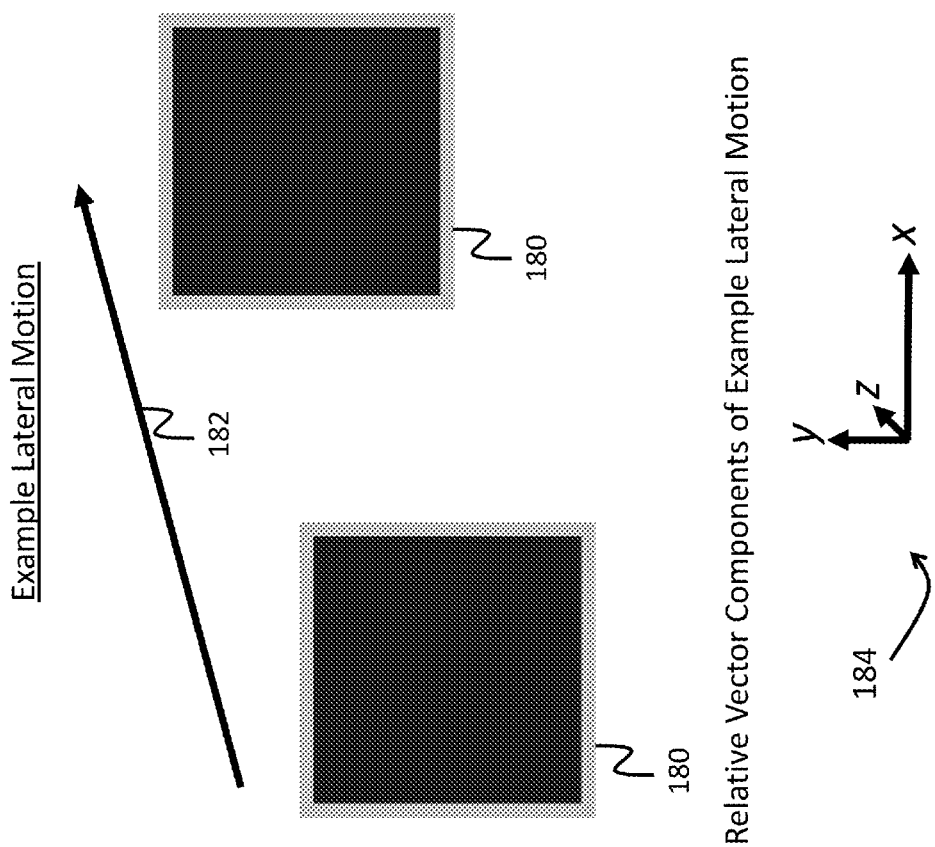

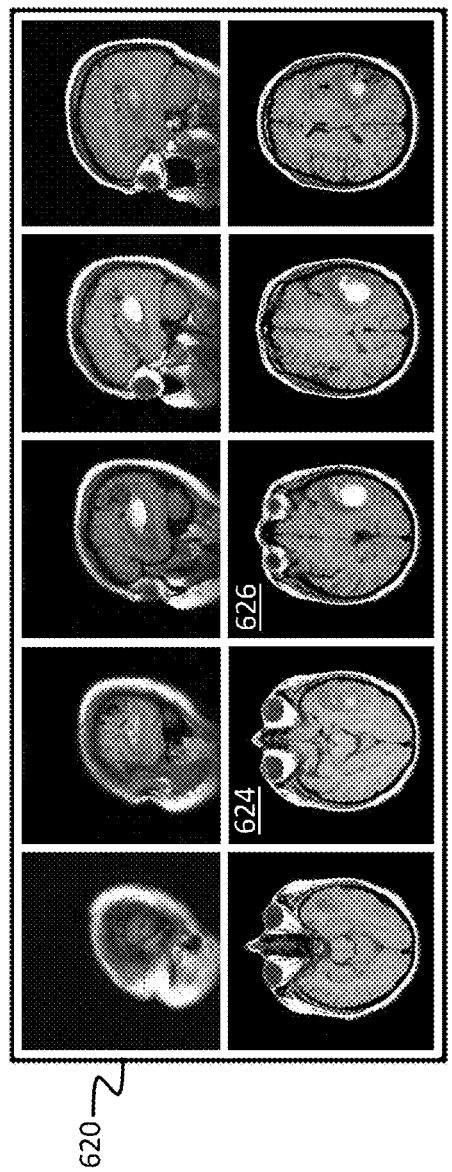
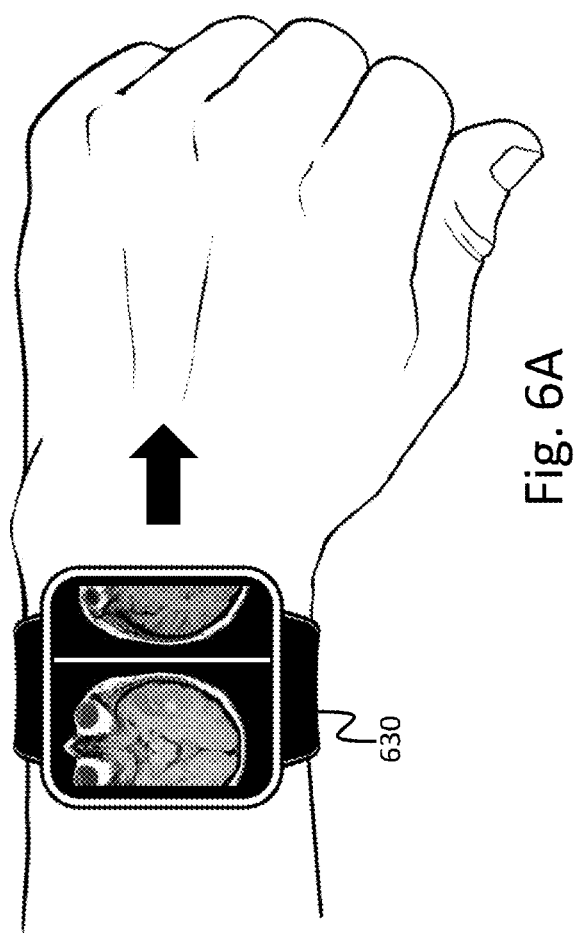
Fig. 6A

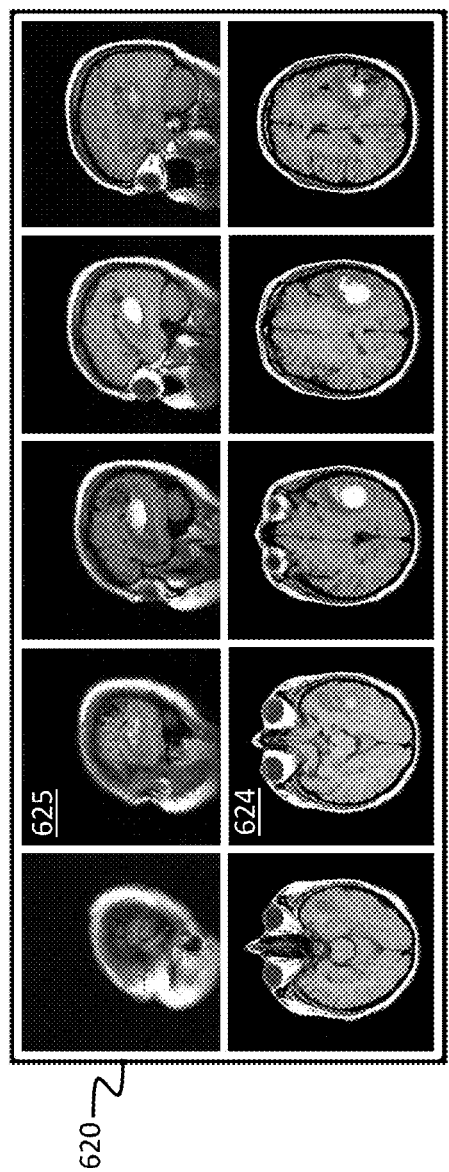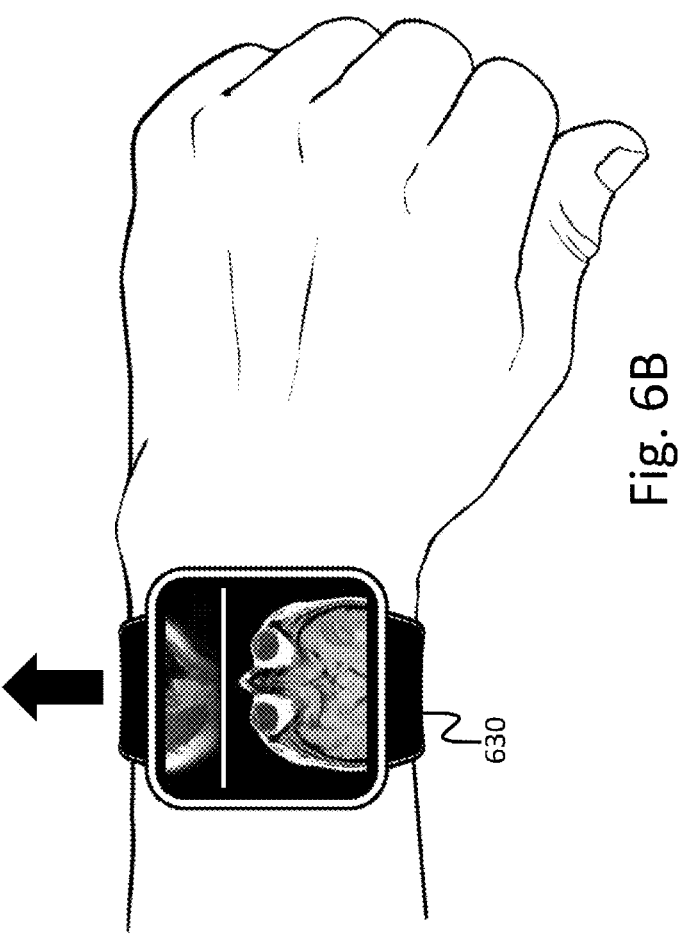
Fig. 6B

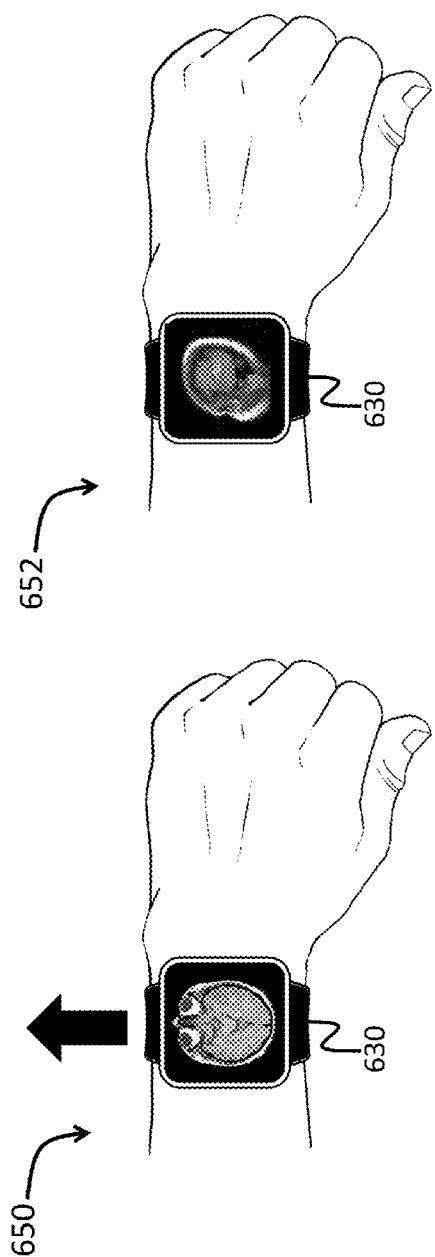
Fig. 6C

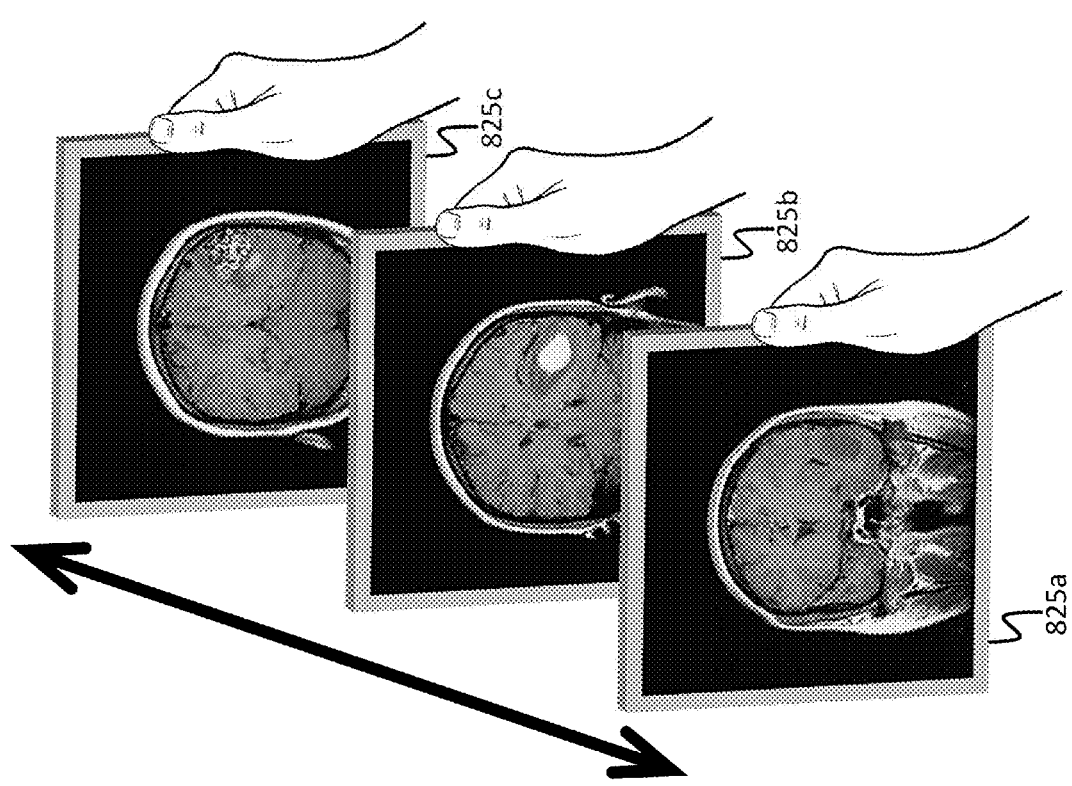

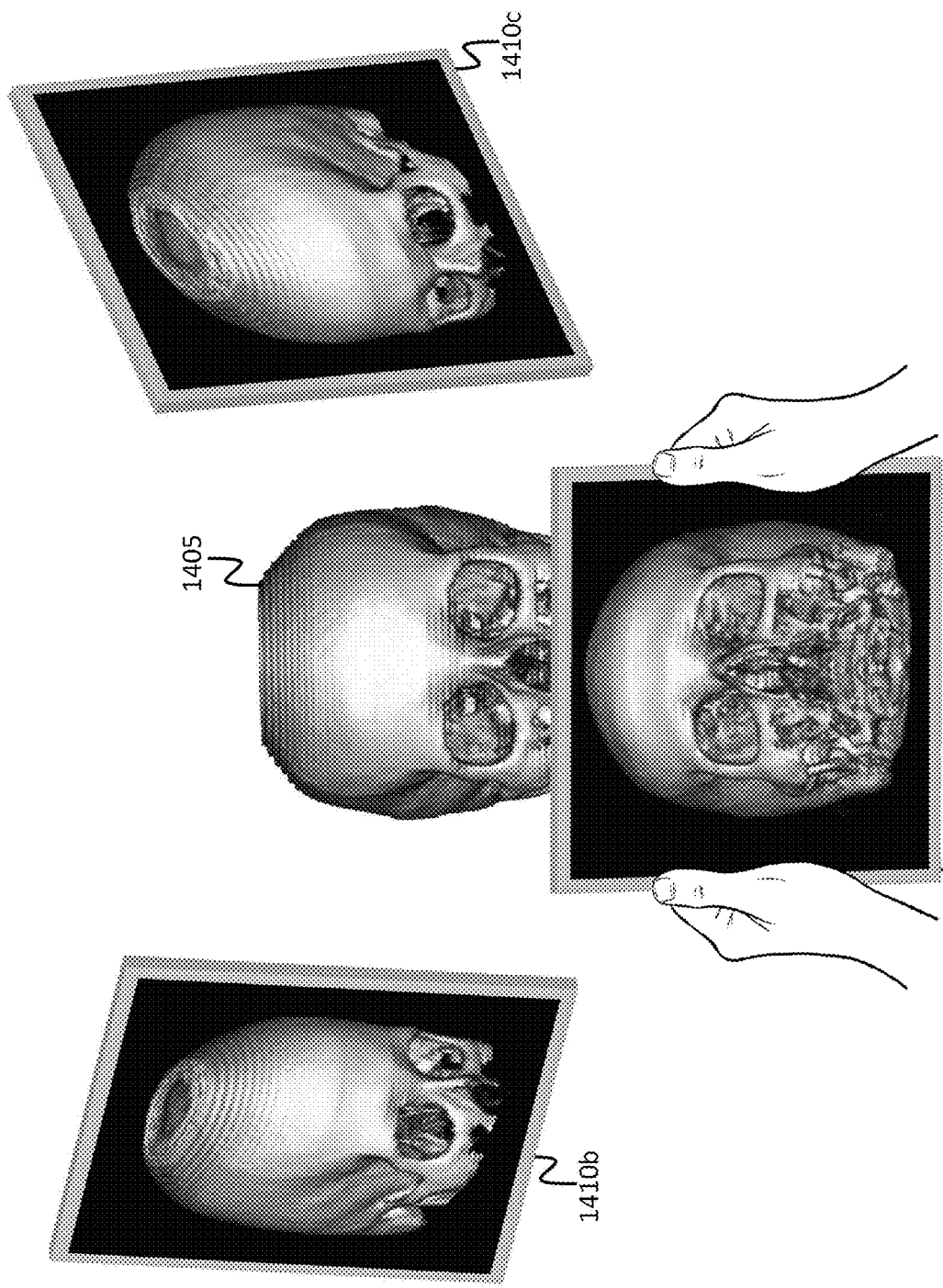

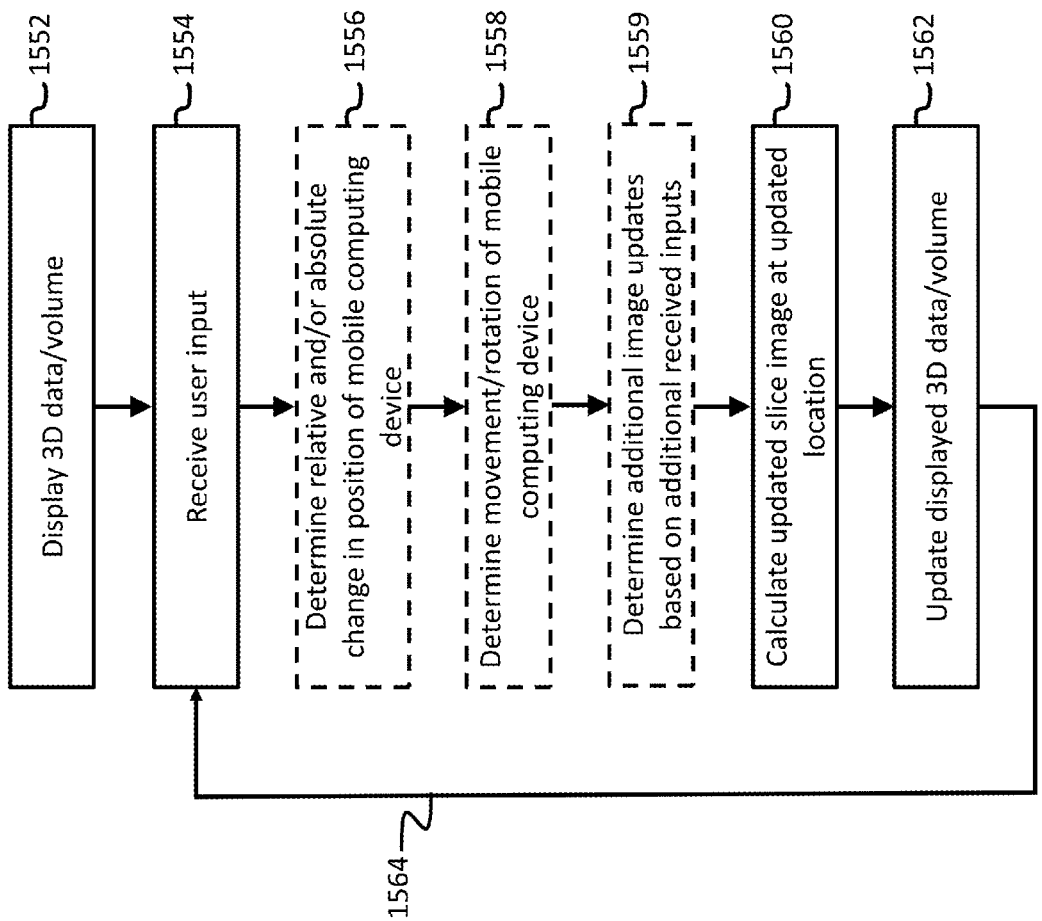

SYSTEMS AND USER INTERFACES FOR DYNAMIC INTERACTION WITH TWO- AND THREE-DIMENSIONAL MEDICAL IMAGE DATA USING SPATIAL POSITIONING OF MOBILE DEVICES

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application No. 61/925,556, filed Jan. 9, 2014, titled "DISPLAY OF PATIENT INFORMATION," and also claims benefit of U.S. Provisional Patent Application No. 61/947,621, filed Mar. 4, 2014, titled "DISPLAY OF MULTI-DIMENSIONAL IMAGE DATA AND PATIENT INFORMATION." The entire disclosure of each of the above items is hereby made part of this specification as if set forth fully herein and incorporated by reference for all purposes, for all that it contains.

TECHNICAL FIELD

Embodiments of the present disclosure relate to systems and techniques for dynamic interactions with medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Many existing vendors offer software that creates and displays images, including the display of color or grayscale images that appear to be three dimensional. In the field of medical imaging, these images are typically based on data describing a volume of material or human tissue. Devices such as CT, MRI, PET, and Ultrasound can generate data describing a volume of human or animal tissue. Caregivers may display these volumes in a manner such that one or more images appear to be three dimensional using techniques such as volume rendering and surface shading. In addition, such software many enable the user to perform multi-planar reconstructions, maximum intensity pixel displays, or display grayscale or color slabs of various thickness and orientations.

Medical images are typically viewed by radiologists and other physicians, patients, and/or others by interaction with desktop computer systems with stationary monitors. Interaction with images in such systems is typically by keyboard and/or mouse input. For example, the reviewing physician may move from one image to the next by pressing an arrow key, movement of the mouse, or movement of the scroll wheel. Such systems are not ideal for at least two reasons. First, medical images may be very large and include significant detail (for example, be very high resolution). Zooming into and scrolling around such images using a keyboard and mouse may be cumbersome, time consuming, and inefficient. Second, medical images are frequently part of a large series of images, or generated from a large amount of three dimensional image data. Moving through such series of images and/or three dimensional image data using a keyboard and mouse may also be cumbersome, time consuming, and inefficient. Mobile devices such as smartphones and tablets may be used to display images, but the difficulties associated with viewing large images and series of images using desktop monitors are made worse by the much smaller size of the displays associated with mobile devices.

SUMMARY

The systems, methods, and devices described herein each have several aspects, no single one of which is solely responsible for its desirable attributes. Without limiting the scope of this disclosure, several non-limiting features will now be described briefly.

Embodiments of the present disclosure relate to systems and techniques for accessing data stores of medical images and displaying the medical images in substantially real-time to provide information in an interactive user interface. As described above, previous systems for display of, and interaction with, image data were typically cumbersome, time consuming, and inefficient for the user. Disclosed herein are systems that, according to various embodiments, advantageously provide highly efficient, intuitive, and rapid dynamic interaction with two- and three-dimensional image data using spatial positioning of mobile devices. The systems may include interactive user interfaces that are dynamically updated to provide a virtual viewbox or window to two- and/or three-dimensional image data. Accordingly, a user may use the systems described herein to more quickly, thoroughly, and efficiently interact with image data including two-dimensional images, three-dimensional image data, and/or series of image data, as compared to previous systems. Additionally, the systems described herein may enable a user to efficiently view and interact with such image data using a small display, such as the display of a smartphone or tablet, rather than requiring a large desktop display. The features and advantages noted above, as well as others, are discussed in further detail below.

Display of and Interaction with, Two-Dimensional Images

According to various embodiments, an image display system is disclosed in which a user may interact with a two-dimensional image, or a series of two-dimensional images (or multiple series of two-dimensional images), via a mobile computing device such as a smartphone, tablet computer, wearable computer (for example, a head-mounted computer), smartwatch, and/or the like. Movement and/or absolute location of the mobile computing device in two- or three-dimensional space may cause display of the two-dimensional image, or the series (or multiple series) of two-dimensional images, to be updated on the mobile computing device. For example, lateral motion of the mobile computing device may cause a corresponding panning of a displayed image (or series of images), display of particular images, and/or selection of an image series. Similarly, other types of motion (including any combination of lateral, translational, and/or rotational motion) of the mobile computing device may cause particular images and/or portions of images (and/or image series) to be displayed. Further, the user may, on-demand, generate a virtual space in which various images and/or image series may be displayed. Accordingly, using the system a user may efficiently view and/or interact with an image (or series of images) having an effective size larger than a viewable area of the display of a mobile computing device.

Display of and Interaction with, Three-Dimensional Images/Data

According to various embodiments, a user of the image display system may interact with a virtual three-dimensional volume or model, or a series of two-dimensional images composed in a virtual three-dimensional space, via a mobile computing device such as a smartphone, tablet computer, wearable computer (for example, a head-mounted computer), smartwatch, and/or the like. Movement and/or absolute location of the mobile computing device in two- or three-dimensional space may cause display of the three-dimensional volume and/or slices of the three-dimensional volume to be updated on the mobile computing device. For example, translational motion of the mobile computing device may cause a corresponding virtual movement toward, away from, and/or through (for example through slices of) a displayed virtual three-dimensional volume. Similarly, rotational motion of the mobile computing device may cause a corresponding virtual rotation of the displayed virtual three-dimensional volume. Further, other types of motion (including any combination of lateral, translational, and/or rotational motion) of the mobile computing device may cause corresponding portions of three-dimensional imaging data to be displayed. Accordingly, using the image display system a user may efficiently view and/or interact with a three-dimensional volume displayed via a mobile computing device.

User Interfaces

It has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface of the mobile computing device described herein may provide an optimized display of image data (both two- and three-dimensional) and may enable a user to more quickly access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including spatial movement of the mobile computing device), translation and delivery of those inputs to various system components, automatic and dynamic execution of complex processes in response to the input delivery, automatic interaction among various components and processes of the system, and automatic and dynamic updating of the user interfaces (to, for example, display the relevant portions of the image data). The interactions and presentation of data via the interactive user interfaces described herein may accordingly provide cognitive and ergonomic efficiencies and advantages over previous systems.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIGS. 1B-1E illustrate an example coordinate system and examples of motion of the mobile computing device.

FIGS. 6A-6C illustrate example user interactions with a series of images via a smartwatch of the image display system, according to an embodiment of the present disclosure.

FIGS. 8-9, 10A-10B, and 11-14 illustrate example user interactions with virtual three-dimensional volumes (or series of two-dimensional images composed in virtual three-dimensional space) via a mobile computing device of the image display system, according to various embodiments of the present disclosure.

FIG. 15 is a flowchart illustrating an example method of the image display system, according to an embodiment of the present disclosure.

DETAILED DESCRIPTION

Figure 1A:
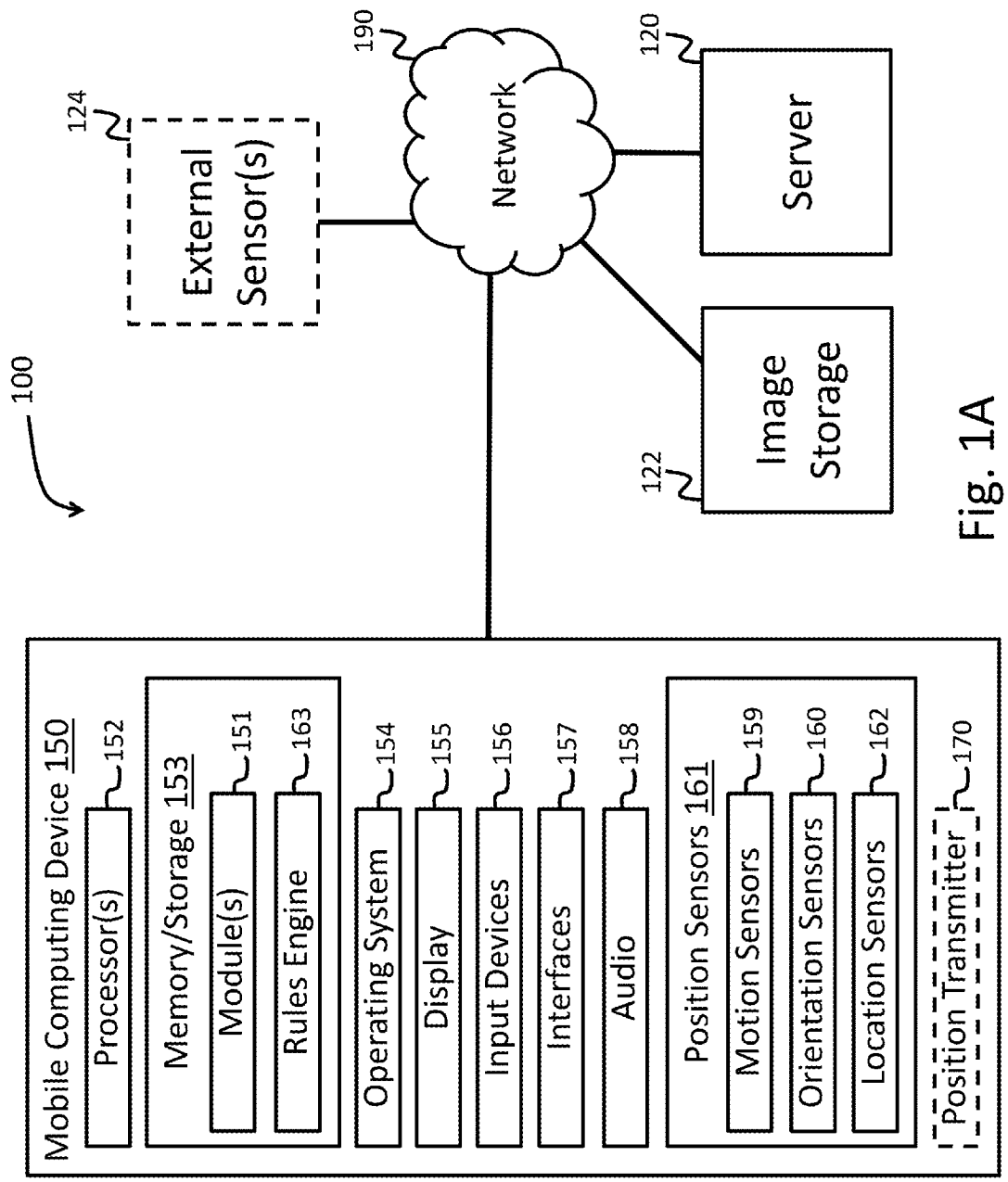
FIG. 1A is a block diagram showing various components of a computing system and network environment in which an image display system may be implemented, according to various embodiments of the present disclosure.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

As mentioned above, according to various embodiments, systems are disclosed that enable a user to more quickly, thoroughly, and efficiently interact with image data including two-dimensional images, three-dimensional image data, and/or series of image data, as compared to previous systems.

As mentioned above, according to various embodiments, an image display system is disclosed in which a user may interact with a two-dimensional image, or a series of two-dimensional images (or multiple series of two-dimensional images), via a mobile computing device such as a smartphone, tablet computer, wearable computer (for example, a head-mounted computer), smartwatch, and/or the like. Movement and/or absolute location of the mobile computing device in two- or three-dimensional space may cause display of the two-dimensional image, or the series (or multiple series) of two-dimensional images, to be updated on the mobile computing device. For example, lateral motion of the mobile computing device may cause a corresponding panning of a displayed image (or series of images), display of particular images, and/or selection of an image series. Similarly, other types of motion (including any combination of lateral, translational, and/or rotational motion) of the mobile computing device may cause particular images and/or portions of images (and/or image series) to be displayed. Further, the user may, on-demand, generate a virtual space in which various images and/or image series may be displayed. Accordingly, using the system a user may efficiently view and/or interact with an image (or series of images) having an effective size larger than a viewable area of the display of a mobile computing device.

Additionally, as mentioned above, according to various embodiments, a user of the image display system may interact with a virtual three-dimensional volume or model, or a series of two-dimensional images composed in a virtual three-dimensional space, via a mobile computing device. Movement and/or absolute location of the mobile computing device in two- or three-dimensional space may cause display of the three-dimensional volume and/or slices of the three-dimensional volume to be updated on the mobile computing device. For example, translational motion of the mobile computing device may cause a corresponding virtual movement toward, away from, and/or through (for example through slices of) a displayed virtual three-dimensional volume. Similarly, rotational motion of the mobile computing device may cause a corresponding virtual rotation of the displayed virtual three-dimensional volume. Further, other types of motion (including any combination of lateral, translational, and/or rotational motion) of the mobile computing device may cause corresponding portions of three-dimensional imaging data to be displayed. Accordingly, using the image display system a user may efficiently view and/or interact with a three-dimensional volume displayed via a mobile computing device.

While the use of medical imaging information is described in the example embodiments herein, in various embodiments the systems and methods described may be used for display of non-medical information, for example, seismic information, weather data, and/or financial data, among others.

Additionally, while the examples herein describe the use of information acquired from a physical object such as a patient, the systems and methods described may be used to display information obtained or generated in other ways, for example, information calculated in a simulation (for example, a financial simulation, and/or a physics simulation, among others). The systems and methods described herein may be used for display of any type of information that can be represented on a digital display.

Figures

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Additionally, in order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Figure 1B:
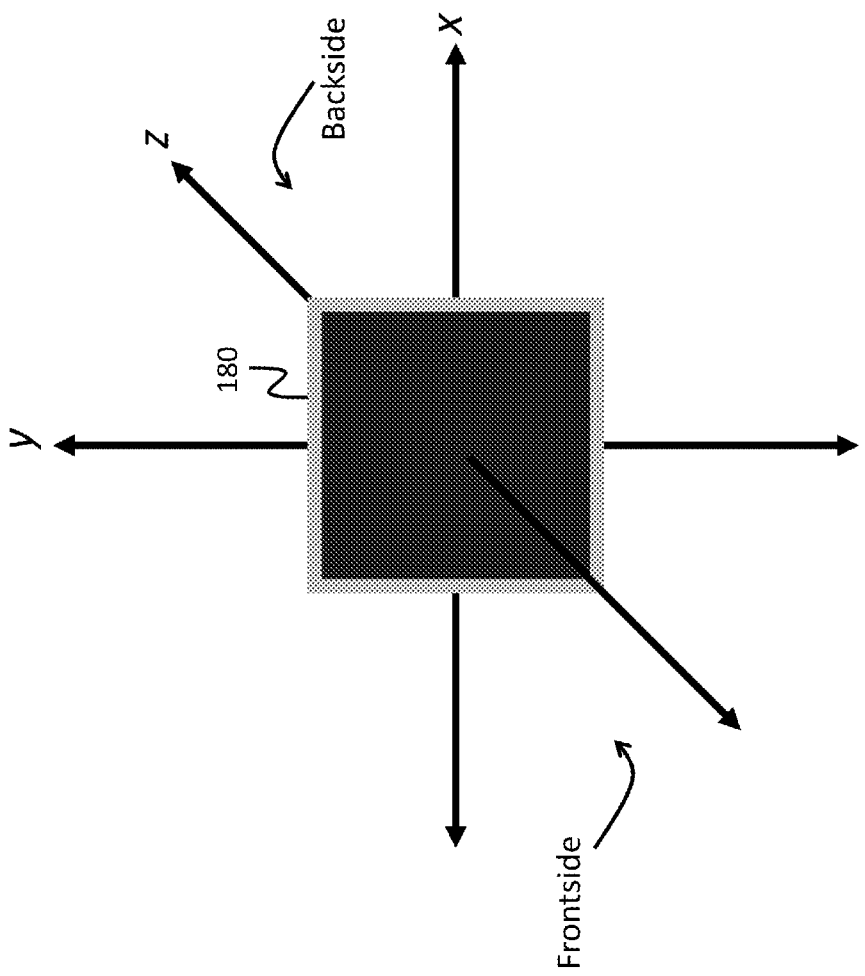
Figure 1D:
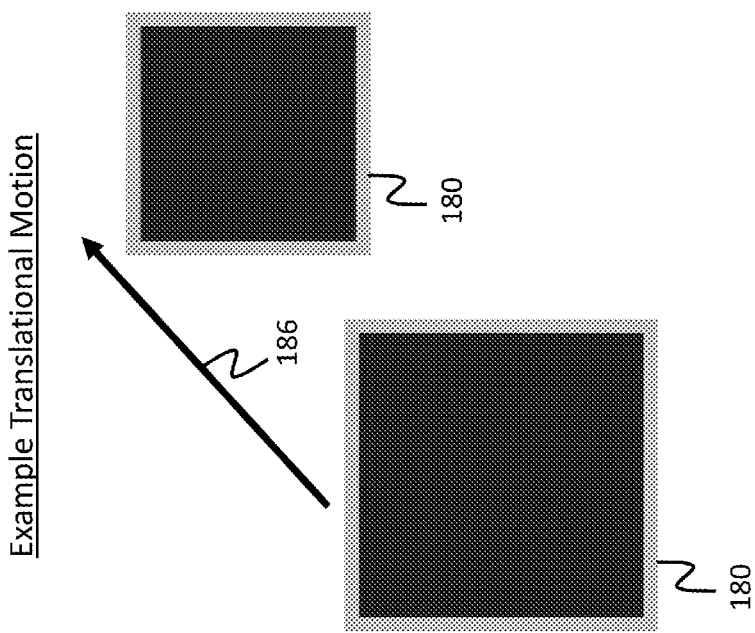
Figure 1E:
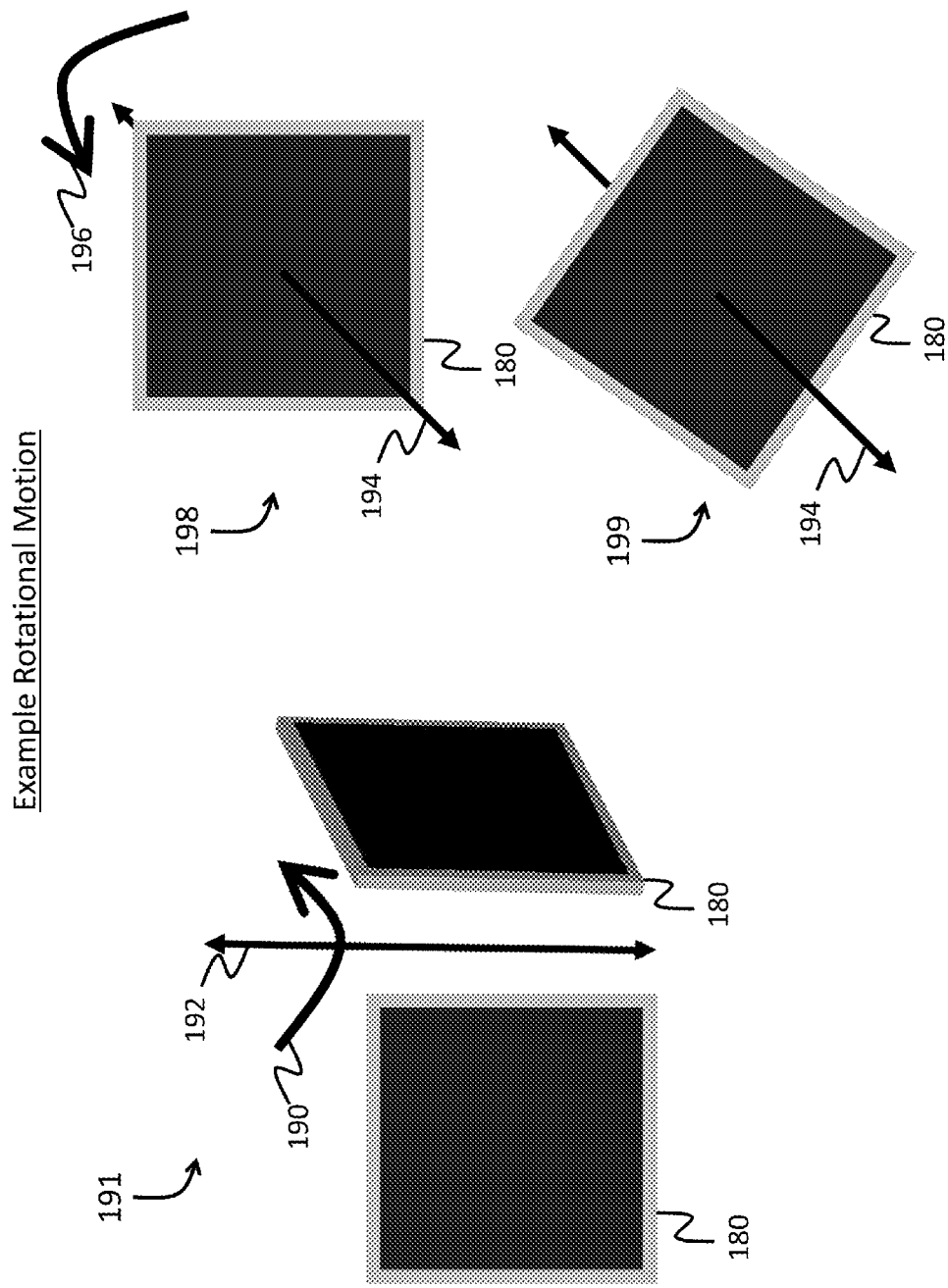

FIGS. 1B-1E illustrate an example coordinate system and examples of motion of the mobile computing device that are useful for providing a common terminology for the present disclosure. Referring to FIG. 1B, a reference three-dimensional coordinate system, relative to a mobile computing device 180, is shown. In particular, the mobile computing device 180 is oriented such that a plane of a display of the device is generally parallel to the x-y plane, and the z-axis is generally perpendicular to the plane of the display. In the description of FIGS. 1C-1E below, the reference three-dimensional coordinate system shown in FIG. 1B is used to describe motion of the mobile computing device 180 from an initial position.

FIG. 1C illustrates an example of what is referred to herein as "lateral" motion of the mobile computing device 180. As shown, the mobile computing device 180 is moved from an initial position to a final position as generally indicated by arrow 182. Diagram 184 illustrates the component vectors (sized relative to one another for illustration purposes) of the example lateral motion. In particular, diagram 184 indicates that the example lateral motion is mostly along the x-axis, and less so along the y- and z-axes. Accordingly, as used herein, "lateral" motion refers to motion of the mobile computing device that is mostly along the x- and/or y-axes, and less so along the z-axis. Thus, while lateral motion may include some motion along the z-axis, a majority (or all in some embodiments) of the motion is comprised of movement along the x- and/or y-axes.

FIG. 1D illustrates an example of what is referred to herein as "translational" motion of the mobile computing device 180. As shown, the mobile computing device 180 is moved from an initial position to a final position as generally indicated by arrow 186. Diagram 188 illustrates the component vectors (sized relative to one another for illustration purposes) of the example translational motion. In particular, diagram 188 indicates that the example translational motion is mostly along the z-axis, and less so along the x- and y-axes. Accordingly, as used herein, "translational" motion refers to motion of the mobile computing device that is mostly along the z-axis, and less so along the x- and/or y-axes. Thus, while translational motion may include some motion along the x- and/or y-axes, a majority (or all in some embodiments) of the motion is comprised of movement along the z-axis.

FIG. 1E illustrates examples of what is referred to herein as "rotational" motion of the mobile computing device 180. As shown, in diagram 191 the mobile computing device 180 is moved from an initial position to a final position, as generally indicated by arrow 190, such that the mobile computing device 180 is rotated about axis 192. In another example the mobile computing device 180 is moved from an initial position illustrated in diagram 198, to a final position illustrated in diagram 199. In this example, as generally indicated by arrow 196, the mobile computing device 180 is rotated about an axis 194 that lies generally along the z-axis with respect to the mobile computing device. In various other examples of rotational motion, the device 180 may be rotated about any other arbitrary axis and/or set of axes. Such an arbitrary axis and/or set of axes of rotation may comprise one or more of an axis that is generally parallel to the x-y plane (e.g., the plane of the display of the mobile computing device) (e.g., as shown in diagram 191), an axis that is generally perpendicular of the x-y plane (e.g., as shown in diagrams 198 and 199), and/or an axis having any other orientation and/or location with respect to the mobile computing device. Further, complex rotational motion may include changes in rotational axes during a rotation. For example, an axis of rotation may be adjusted to compensate for incidental movements of the mobile computing device 180 outside of a strict rotational motion around the axis of rotation as positioned at a start of the rotational motion. Accordingly, as used herein, "rotational" motion refers to motion of the mobile computing device that includes rotation about any axis, or set of axes.

In various embodiments of the disclosure, motion of the mobile computing device may include one or more of lateral, translational, and rotational motion. For example, a rotational movement of the mobile computing device by a human user generally also includes some translational and/or lateral motion due to the way a human's arm moves. Similarly, a lateral movement of the mobile computing device by a human user generally also includes some rotational and/or translational motion due to a human's physiological limitations. While various examples disclosed herein may refer to one or more particular types of motion, in various embodiments other types of motion, and/or combinations of motion, may be used to accomplish the functionality described.

The term "angular" motion may be used herein to refer to generally lateral, and slightly rotational, movement of the mobile computing device by a human user in an arc (for example, by holding the mobile computing device by an arm and sweeping it across a front of the user's body).

The term "position" as used herein is a broad term and has its ordinary and customary meaning, including without limitation location, orientation, rotation, angle, alignment, and/or the like. A position may be relative to a reference and/or absolute. For example, when used in reference to a physical object (for example, a mobile computing device), a "position" of the physical object may include, without limitation, the physical object's location, orientation, rotation, angle, and/or alignment. When used in reference to a virtual object (for example, an image located in a virtual space), a "position" of the virtual object may include, without limitation, the virtual object's location, orientation, rotation, angle, and/or alignment. When used in reference to electronic image data, a "position" within the image data (for example, a position in a two-dimensional image, a position in three-dimensional image data, a position in a series of images, and/or the like) may include, without limitation, the location, orientation, rotation, angle, and/or alignment of and/or within the image data. A relative position refers to a position that is determined relative to a starting reference position. An absolute position refers to a particular position in space that may be determined independent of any starting position.

FIG. 1A is a block diagram showing various components of a computing system and network environment 100 in which the image display system (which may be referred to herein as "the display system" or simply "the system") may be implemented, according to various embodiments of the present disclosure.

As shown, the computing system 100 may include a mobile computing device 150, a computer network 190, an image store 122, a server 120, and/or one or more optional external sensors 124. As described below, in various embodiments the mobile computing device 150, the image storage 122, the server 120, and/or the external sensor(s) 124 may be in communication with one another via the network 190. Additionally, the mobile computing device 150 may include various components as shown and described in detail below.

In various embodiments, mobile computing device 150 may be a smartphone, a tablet computer, a wearable computer (for example, a head-mounted computer and/or a computer in communication with a head-mounted display), a smartwatch, and/or the like. As described below, the mobile computing device 150 may display images and/or patient information to a user via a display 155. Further, user input may be received via the mobile computing device 150, for example movement and/or location information associated with the mobile computing device 150, in response to which the information displayed may be updated.

Figure 2:
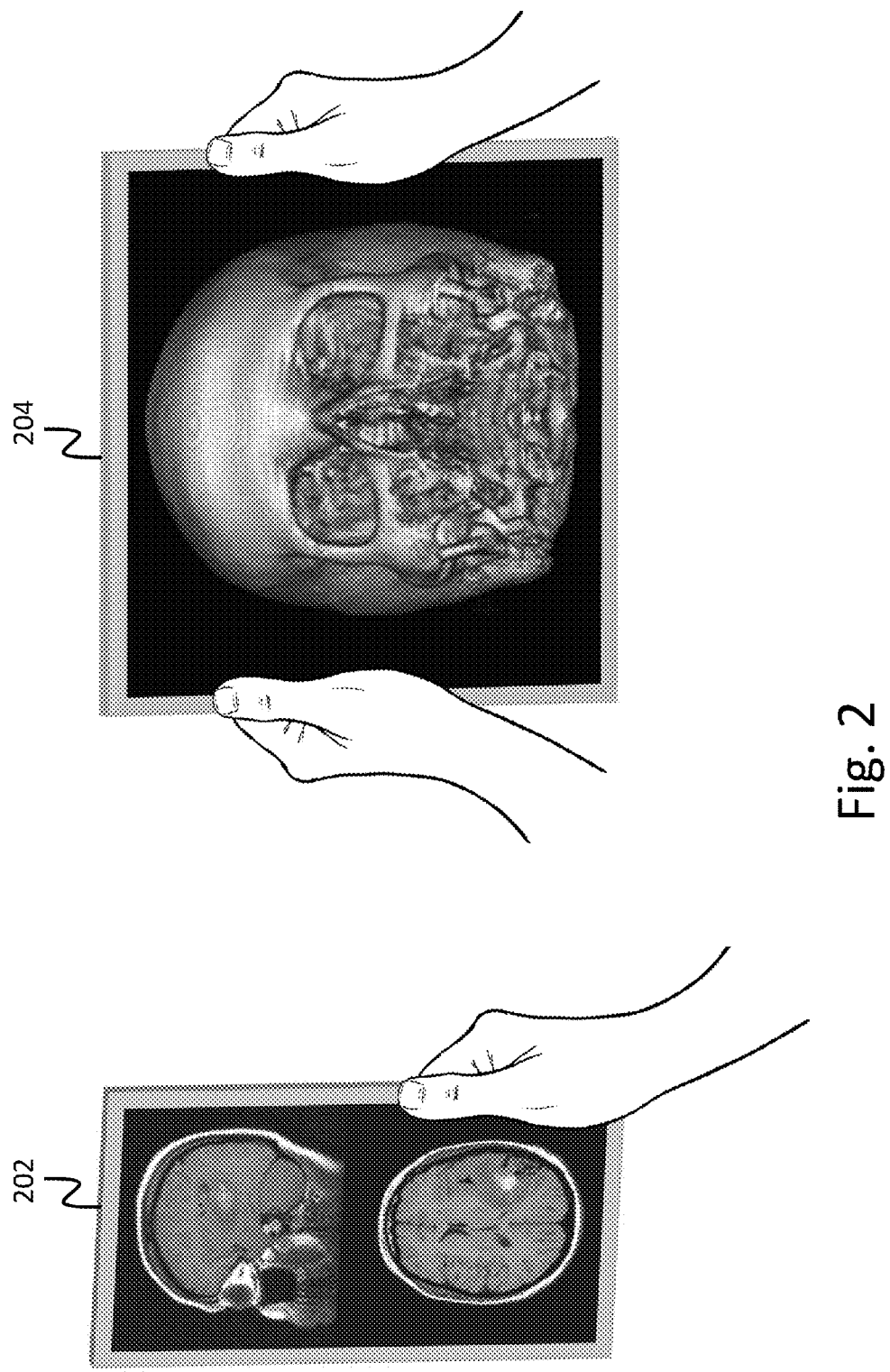
FIGS. 2-4 illustrate various examples of mobile computing devices that may be used in conjunction with the image display system, according to various embodiments of the present disclosure.
Figure 3:
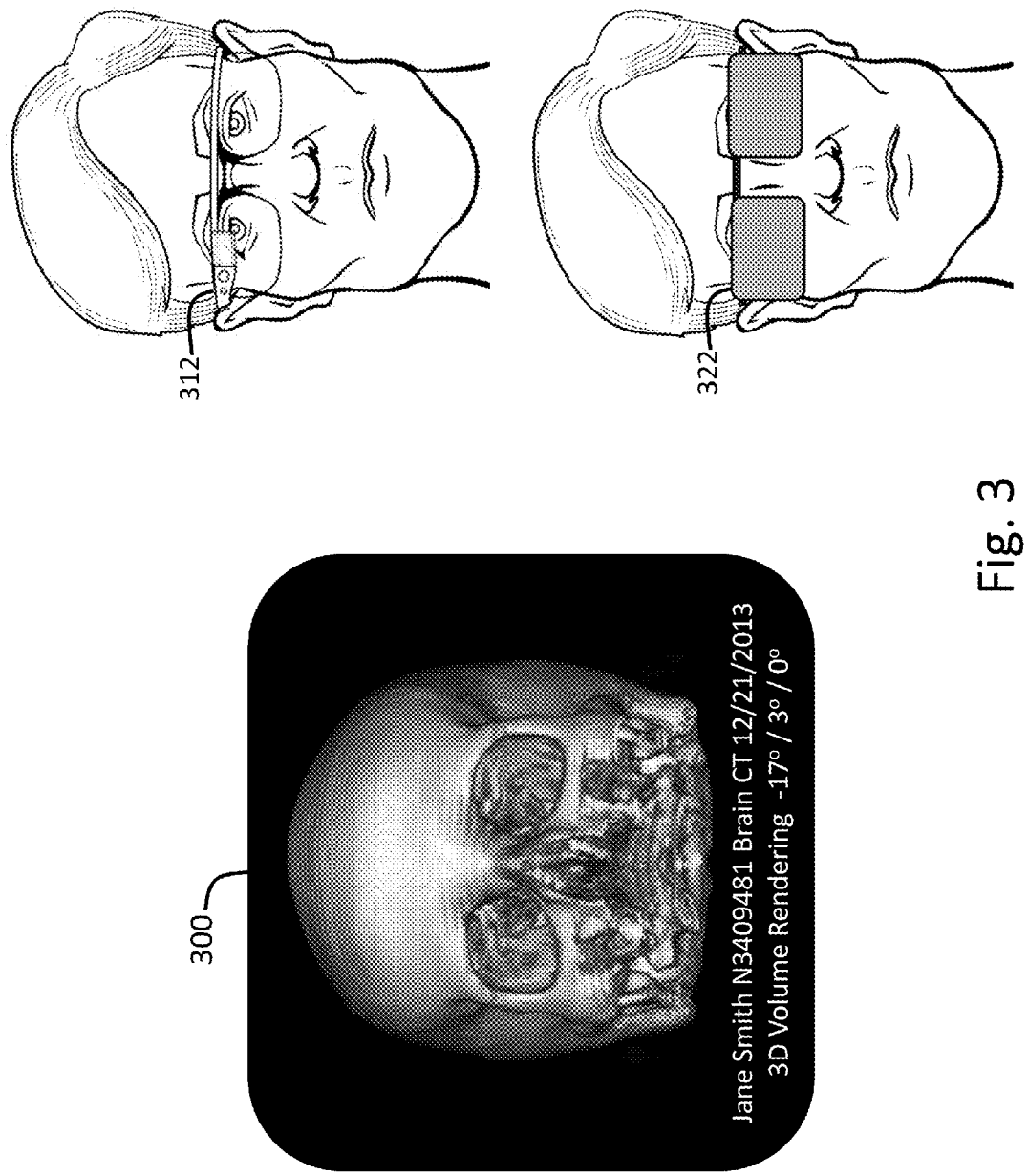
Figure 4:
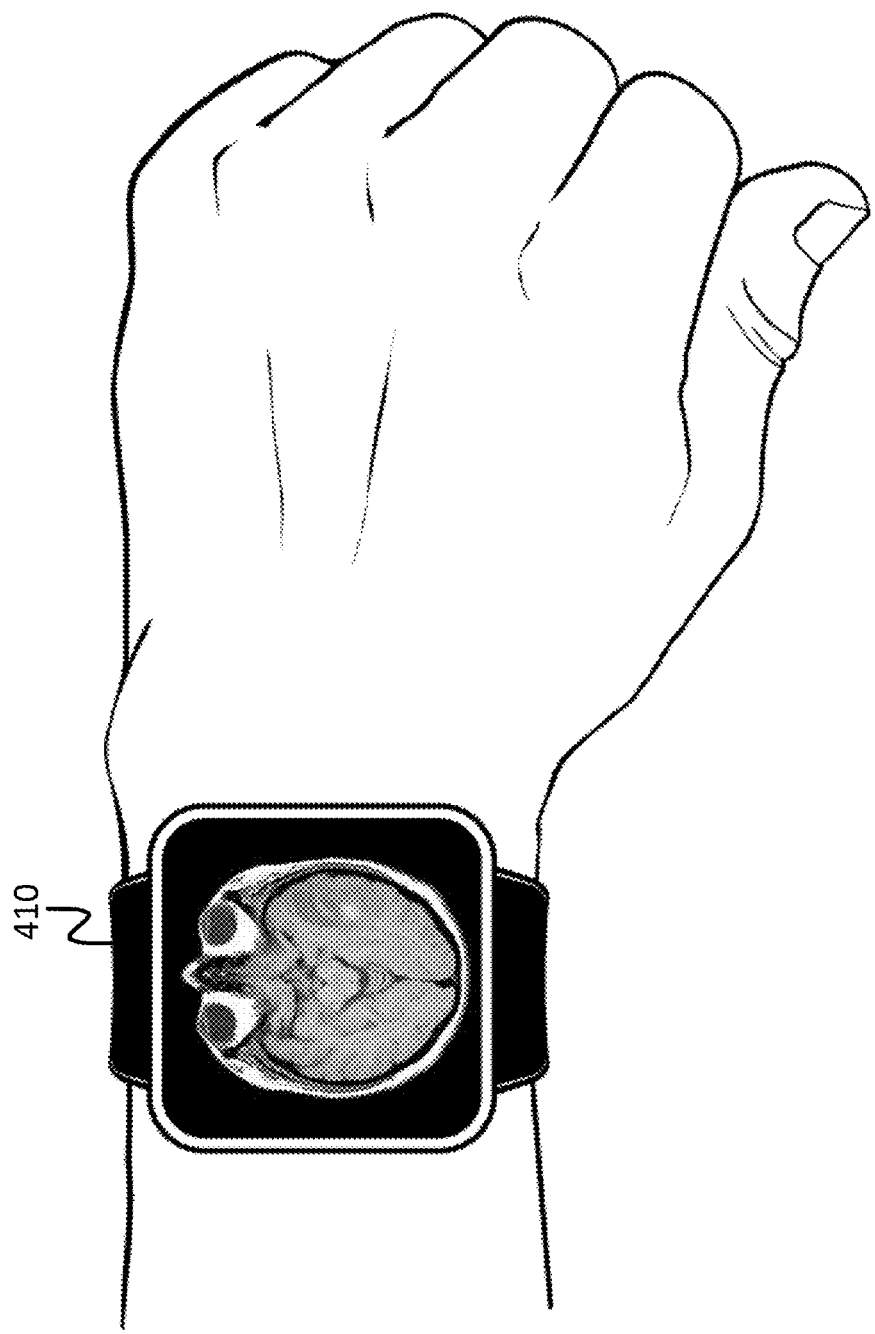

FIGS. 2-4 illustrate various examples of mobile computing devices that may be used in conjunction with the system, according to various embodiments of the present disclosure. For example, the mobile computing device 150 may be a handheld device, such as smartphone 202 or tablet 204 illustrated in FIG. 2. In other embodiments mobile computing device 150 may be a wearable display device or computer that projects visual information into the user's visual field, such as head mounted wearable computer 312 illustrated in FIG. 3. In other embodiments, mobile computing device 150 may be another form of a wearable computer, such as a computer in the form of a smartwatch 410, illustrated in FIG. 4 and capable of displaying visual information.

Referring to FIG. 3, an example mobile computing device in the form of a wearable computer 312 that contains a display that is projected into the user's visual field is illustrated. FIG. 3 further illustrates an example of information 300 that may be displayed to the user from a wearable computer providing a heads-up display, such as example wearable computer 312. In other examples of wearable computers with displays, the display may occupy essentially the entire visual field of the user, such as virtual reality display 322, and/or the display may be in communication with a computing device that is in a separate location than, for example, virtual reality display 322.

Referring again to FIG. 1A, as described mobile computing device 150 may include various components, including those illustrated in FIG. 1A (and described in further detail below). For example, components of the mobile computing device 150 may include one or more processors 152 and memory and/or data storage 153 (including one or more software modules 151 and/or a rules engine 163 (which may itself comprise a software module)). In particular, as described below, the rules engine 163 may execute various rules that may be used to translate an amount of movement of the mobile computing device 150 into a corresponding movement through the imaging volume or series of images. Such a determination may be based on, for example, an image type. Components may also include position sensors 161, which may include, for example, motion sensors 159, orientation sensors 160, and/or location sensors 162. The various position sensors 161 may include, for example, gyroscopes (that may be used, for example, to detect and measure rotational motion), accelerometers (that may be used, for example, to detect and measure linear motion), cameras, Global Positioning System (GPS) transceivers and devices, near field communication (NFC) technology devices, Radio Frequency Identification (RFID) devices, systems and devices utilizing WiFi, systems and devices utilizing Bluetooth such as iBeacons, and/or the like. The mobile computing device may also include an optional position transmitter 170 that may be used in combination with external sensors 124 to track the location, position, movement, and/or orientation of mobile computing device 150. The various sensors and transmitters may provide input/data to the mobile computing device 150, and may also transmit such data, related to the device's position, including the device's location, orientation, and/or motion. Such information may be processed by, for example, one or more software modules of the mobile computing device and/or other components of the system, as described below, such that displayed image data may be updated.

Additionally, in some embodiments the network environment 100 includes the one or more external sensors 124 which may provide information to the system to determine the position (including, for example, the location and/or orientation) of mobile computing device 150. The external sensors 124 may include, for example one or more cameras (for example, video and/or infrared cameras), NFC technology devices, RFID devices, iBeacons, and/or other position sensors such as any of the position sensors 161 described above. In an embodiment, the external sensors 124 include an array of cameras capable of detecting (and/or providing data necessary for detecting) a position (including a location and/or orientation) of the mobile computing device. For example, the external sensors 124 may comprise a commercially available position sensor such as Microsoft's Kinect or Leap Motion's Leap Motion Controller. In an embodiment, as mentioned above, the position transmitted 170 may transmit a position of the mobile computing device to one of the external sensors 124. In some embodiments position information from the external sensors 124 may supplement position information from the position sensors 161. In other embodiments, a location of the mobile computing device 150 may be determined based on only information from position sensors 161 or based on only information from external sensors 124.

As further described below, computing system 100 may include a server 120 that provides information that is displayed by computing device 150. Computing system 100 may include image storage 122 (for example, a data store, database, or storage system) that may be configured to store information, such as image data (also referred to herein as image and/or imaging information) (for example, images, image series, three-dimensional imaging data, and/or the like), that is processed by server 120 and/or mobile computing device 150. In various embodiments, the functionality provided by image storage 122 and/or server 120 may reside within mobile computing device 150. The term "database," as used herein, may refer to a database (for example, RDBMS, or SQL, or NoSQL database), or may refer to any other data structure, such as, for example a comma separated values (CSV), eXtendible markup language (XML), TeXT (TXT) file, flat file, spreadsheet file, and/or any other widely used or proprietary format.

Display of and Interaction with, Two-Dimensional Images

When a person needs to view and navigate through large amounts of information, they may use desktop computing systems with one or more large computer monitors and input devices such as a keyboard and trackball. For example, a doctor that needs to view a large medical imaging exam or a large amount of information on a patient within an electronic medical record (EMR) system may use a desktop computer rather than a mobile device, because such a computer may be more efficient than attempting to view the information on a mobile device. However, in many situations such relatively large computing devices (for example, desktop computers with a keyboard and mouse) may not be available, not practical, and/or not desirable for reviewing medical images.

Advantageously, the present disclosure describes methods and systems that may enable a user to efficiently view and navigate through large imaging exams and/or other information by moving a mobile computing device. According to various embodiments, a user may use the image display system to interact with a two-dimensional image, or a series of two-dimensional images (or multiple series of two-dimensional images), via a mobile computing device. As described below in reference FIGS. 5, 6A-6E, and 7A-7B, movement and/or location of the mobile computing device in two- or three-dimensional space may cause display of the two-dimensional image, or the series (or multiple series) of two-dimensional images, to be updated on the mobile computing device. For example, lateral motion of the mobile computing device may cause a corresponding panning of a displayed image (or series of images), display of particular images, and/or selection of an image series. Similarly, other types of motion (including any combination of lateral, translational, and/or rotational motion) of the mobile computing device may cause particular images and/or portions of images (and/or image series) to be displayed. Further, the user may, on-demand, generate a virtual space in which various images and/or image series may be displayed. Accordingly, using the system a user may efficiently view and/or interact with an image (or series of images) having an effective size larger than a viewable area of the display of a mobile computing device.

Figure 5:
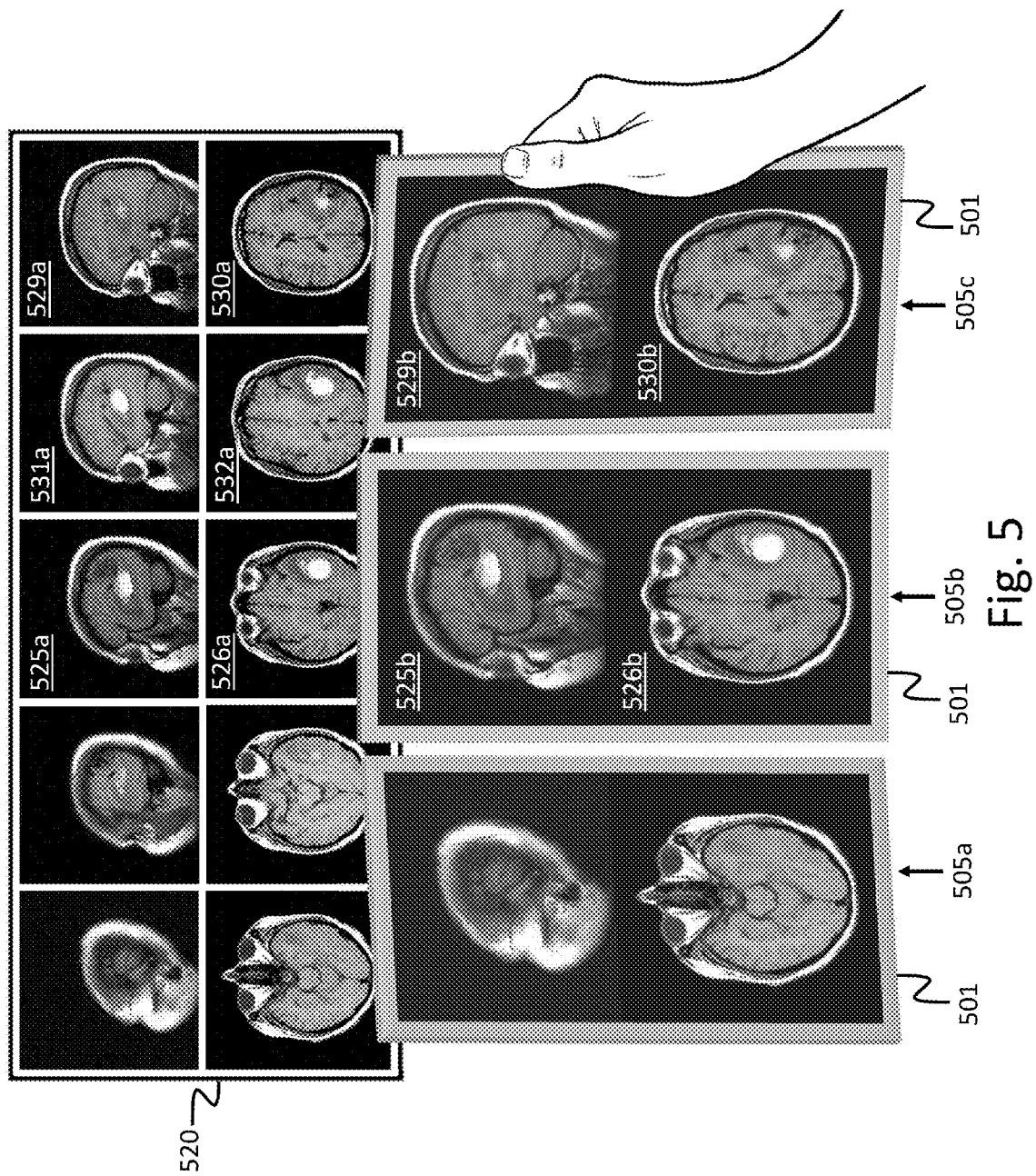
FIG. 5 illustrates example user interactions with a series of images via a smartphone of the image display system, according to an embodiment of the present disclosure.

FIG. 5 illustrates example user interactions with a series of images via a smartphone 501 of the image display system, according to an embodiment of the present disclosure. As mentioned above, the mobile computing device 150 may be a smartphone capable of displaying images and receiving inputs from a user.

In the embodiment of FIG. 5, the user may navigate a series or array of images 520 that are significantly larger than may be displayed on the display of the mobile device (in this example, the smartphone 501). In this example, image array 520 represents an array of images that in conventional imaging viewing systems might be displayed on one or more large desktop computer monitors. In the embodiment displayed, this array of images 520 is virtual, meaning it is not concurrently displayed in the form illustrated on one or more physical monitors. Rather, as shown, the user is viewing parts of the virtual image array 520 via the smartphone 501, which acts to provide a type of virtual viewbox to the virtual image array. As explained further below, the virtual viewbox allows the user to view a portion of the virtual image array 520, such as a portion that can be adequately displayed on the particular display of the device, such as a portion of the virtual image array 520 that can be displayed at a minimum resolution that the user of the device has indicated is necessary to properly analyze images of the virtual image array 520.

FIG. 5 illustrates an example of the user holding smartphone 501 (which, in other embodiments may be a tablet or other mobile computing device) in three physical positions: 505*a*, 505*b*, and 505*c*. As the user physically moves the mobile computing device into different positions (e.g., physical location and/or orientation), the change in device position is sensed, and different images from the virtual image array 520 are automatically displayed on the display of the mobile device.

For example, when the smartphone 501 is in a first relative position 505*b*, images 525*b* and 526*b* (correlating with images 525*a* and 526*a* of the image array 520) are displayed on the smartphone 501. When the smartphone 501 is moved to the right to a second relative position 505*c* (e.g., moved laterally and rotated slightly), images 529*b* and 530*b* (corresponding to images 529*a* and 530*a* of the image array 520) are displayed on the smartphone 501. Similarly, the smartphone 501 may be moved to a third relative position located between the first and second relative positions to display images corresponding to images 531*a* and 532*a*.

In various embodiments, the various different sensors of the mobile computing device 150 may be used to determine motion of the device and/or a position of the device. Then, the location and/or motion may be used by the image display system to determine which images (or portions of images) to display on the mobile computing device. For example, in one embodiment, the position (for example, the location and/or orientation) of smartphone 501 is used as input to determine which images of the virtual image array to display. In another embodiment, the motion of smartphone 501 may be used as input. In another embodiment, the orientation of the smartphone 501 may be used as input. As shown and described in reference to FIG. 5, the movement/change of images displayed on the mobile computing device may be correlated with the motion of the device. For example, a movement of the mobile computing device a particular distance to the left (e.g., a lateral motion) may cause a correlated translation, panning, or movement of the displayed images to the right. In an embodiment, the correlated movement of the images may be proportional to the motion of the mobile computing device.

In various embodiments, such translation, panning, or movement of the displayed images may be correlated with angular motion of the mobile computing device. For example, the system may enable a user to stand in one place and sweep the device in an arc, left-right and up-down, to view images that are positioned relative to one another. For example, by measuring angular motion of the mobile computing device, the user may sweep the device up-down to see images above and below a current view, and sweep the device left-right (e.g., rotate the device, or simply rotate left-right in an office chair) to see virtual images to the left and right.

In some embodiments, translational and/or rotational motion of the mobile computing device may be ignored when determining which images to display on the mobile computing device in response to lateral motion.

FIGS. 6A-6C illustrate example user interactions with a series of images via a smartwatch of the image display system, according to an embodiment of the present disclosure. As mentioned above, the mobile computing device 150 may be a smartwatch capable of displaying images and receiving inputs from a user. In the example illustration of FIGS. 6A-6C, a virtual image array 620 is shown that is similar to the virtual image array 520 of FIG. 5. The virtual image array 620 may not actually be displayed to the user in its entirety on a large display, but is shown in the figure for illustrative purposes.

In FIG. 6A smartwatch 630 is worn by a user who is currently viewing image 624 and is moving the smartwatch laterally to the right. In the example, in response to the lateral motion of the smartwatch, a virtual viewbox of the image array is moved from displayed image 624 to image 626, as shown. In FIG. 6B, with the user viewing image 624, a lateral motion of the smartwatch in an upward direction causes the virtual viewbox of the image array to move towards display of image 625, as shown. Further, as shown in FIGS. 6A-6B, in an embodiment the system may smoothly scroll from one portion of the virtual image/image array to a next portion. In another embodiment, as shown in FIG. 6C, the system may "snap" to particular portions/images. For example, as shown, in response to a lateral motion of the smartwatch in an upward direction (as shown in diagram 650), the virtual viewbox of the image array is "snapped" from displayed image 624 to image 625 (as shown in diagram 652). In this embodiment, animation from one image to another may be omitted (or may be reduced to show just a first 5-10 percent movement in of an adjacent image on a side of the display prior to snapping to the adjacent image). In various embodiments other images may be displayed in response to changes in position (for example, location and/or orientation) of the smartwatch using, for example, inputs related to position, motion, orientation, and/or location. As described above in reference to FIG. 5, the movement/change of images displayed on the mobile computing device may be correlated with the motion of the device.

Figure 6D:
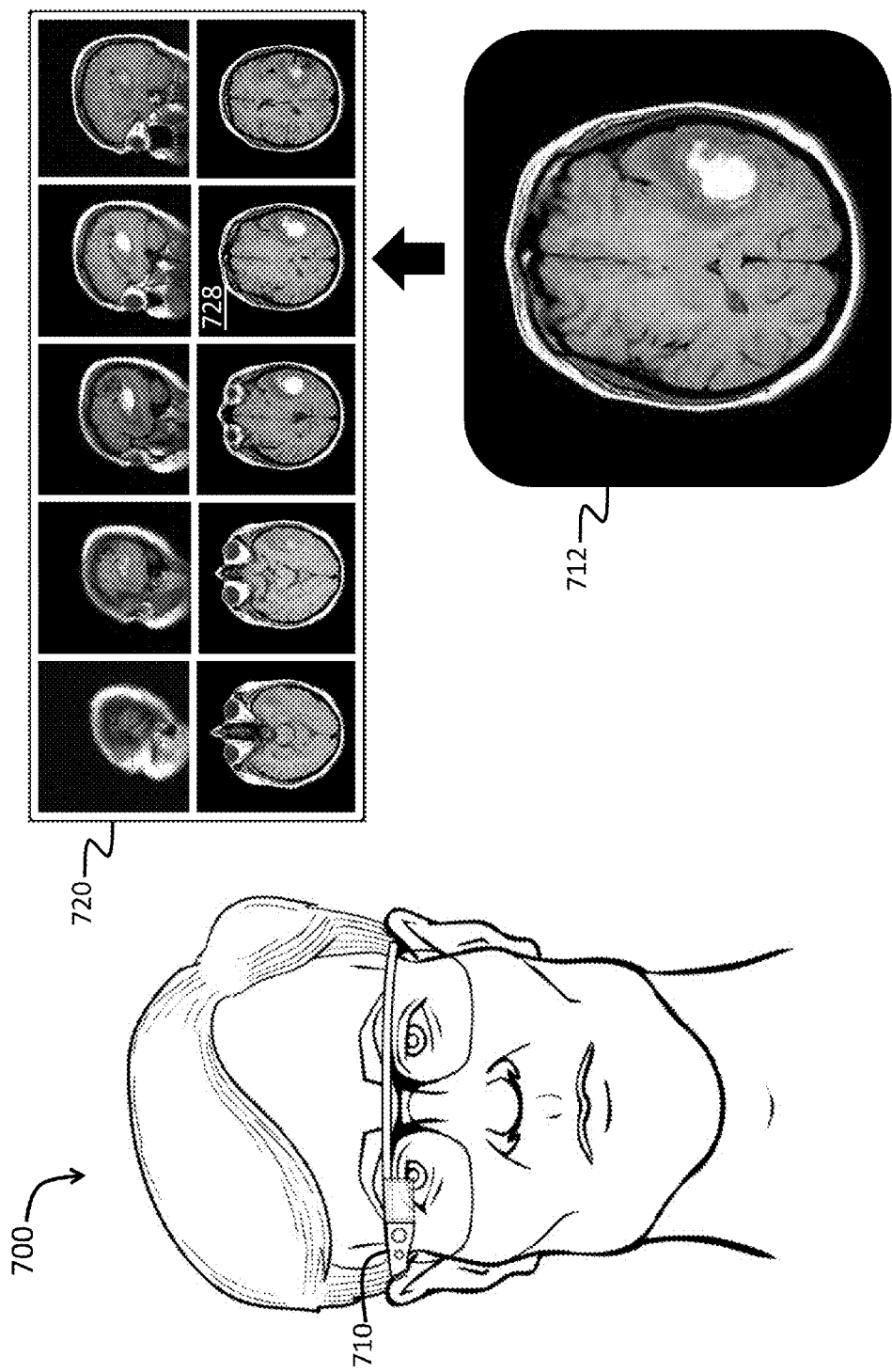
FIG. 6D illustrates example user interactions with a series of images via a head-mounted computing device of the image display system, according to an embodiment of the present disclosure.

FIG. 6D illustrates example user interactions with a series of images via a head-mounted computing device 710 of the image display system, according to an embodiment of the present disclosure. As mentioned above, the mobile computing device 150 may be a wearable computing device capable of displaying images and receiving inputs from a user. As with FIGS. 6A-6C, in the example illustration of FIG. 6D a virtual image array 720 is shown that is similar to the virtual image array 520 of FIG. 5. The virtual image array 720 may not be displayed to the user in its entirety on a large display, but it is shown in the figure for illustrative purposes.

In FIG. 6D, the head-mounted computing device 710 is worn by a user 700, and is a wearable computer with a heads-up display, virtual reality display, and/or other display system that projects visual information into the user's visual field. In the example illustration, mobile device/head-mounted computing device 710 is displaying visual information 712 to the user's visual field (in this example an image 728 from virtual image array 720). As in the example embodiment of FIG. 5, other images (or portions of images) are automatically displayed in response to sensor input, for example, motion and/or changes in position (including, for example, orientation, and/or location).

While the example image arrays 520, 620, and 720 illustrated in FIGS. 5 and 6A-6D comprise a 5×2 array of images, image arrays may consist of any arbitrary size, for example, a 10×8 array of images.

In an embodiment, the image frames in a virtual image array may represent images of an image series. For example, image 525a in image array 520 may represent one of many (for example, 10, 20, 40, 50, or more) images in a series of images, for example a sagittal T1 series from a brain MRI, consisting of sequential parallel images through a patient's brain. In an embodiment, user input, for example in the form of multitouch input on the mobile device's screen and or rotation of a knob, dial, and/or crown of the mobile device, may allow the user to navigate through images within the series. In an embodiment, each frame of a virtual series may represent a different image series. Movement of the mobile computing device may be used to select different series to display on the mobile device (e.g., via lateral and/or translational movement of the mobile computing device), and multitouch input on the mobile device's screen may be used to navigate through images in the selected series. These aspects of the system are described in further detail in reference to FIG. 6E.

Figure 6E:
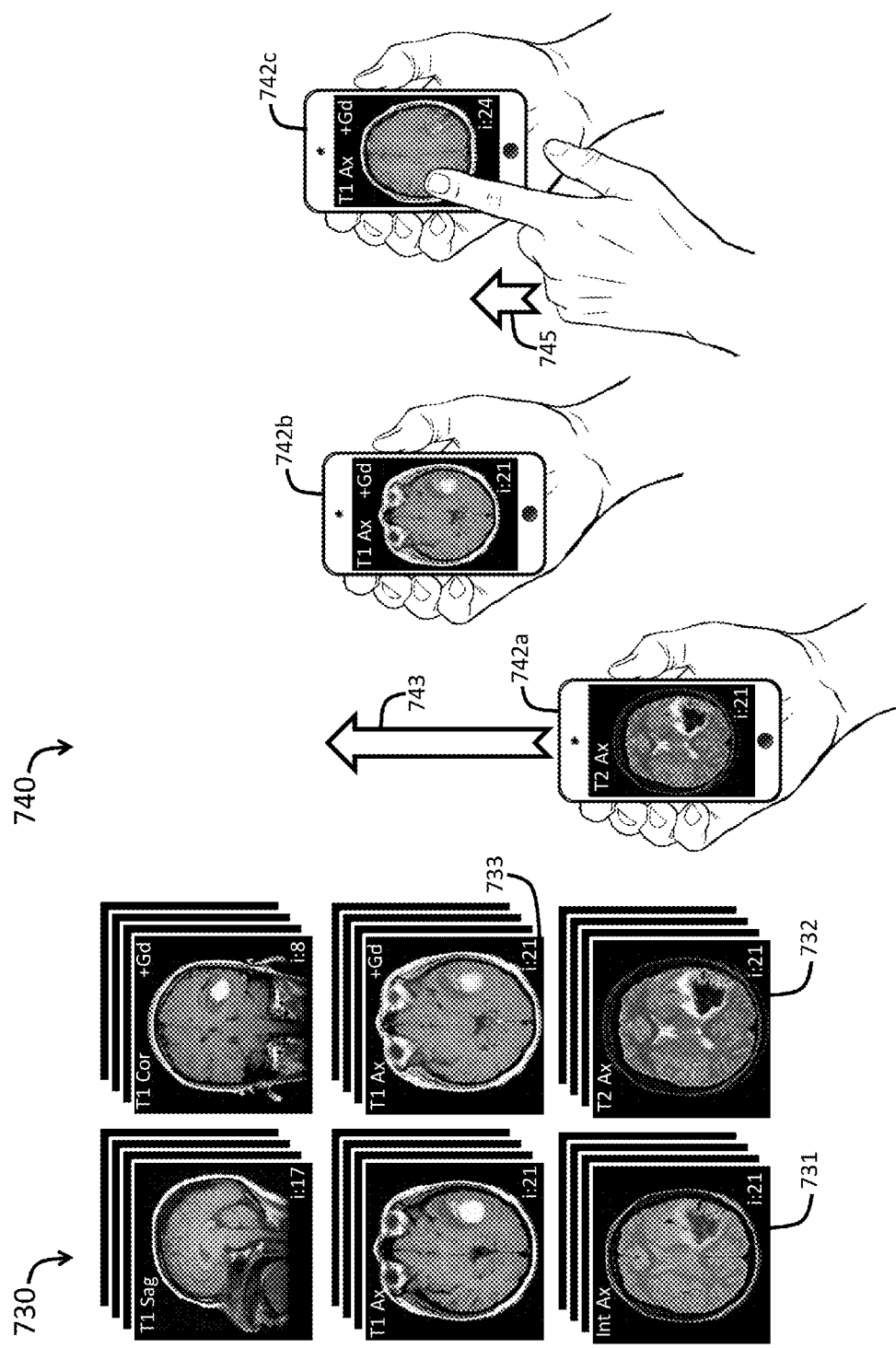
FIG. 6E illustrates example user interactions with multiple series of images via movement and interaction with a smartphone of the image display system, according to an embodiment of the present disclosure.

FIG. 6E illustrates example user interactions with multiple series of images (as shown in diagram 730) via movement and interaction with a smartphone (as shown in diagram 740) of the image display system, according to an embodiment of the present disclosure. In the embodiment shown in FIG. 6E, each image position in a virtual array (as shown in diagram 730) may represent a series of images. As described above and below, the user may move the mobile computing device (e.g., a smartphone) to select among the series. Further, once a series is selected, a user may display different images within the selected series via interaction with the mobile computing device (as described in further detail below).

In medical imaging, many modalities (e.g., MRI, CT, and PET) create series of images, where each series of images may consist of a group of parallel images at sequential spatial locations with respect to the patient. Different series may be acquired at different times, in different orientations, and/or may differ in various ways. For example, one series may be acquired with different imaging parameters than another, and series may be acquired before or after administration of contrast material.

In FIG. 6E, diagram 730 shows a virtual array of images where each position, represented by an image, represents a series of images, with other images within the same series schematically shown behind the displayed image. Each of the image series may include any number of images. In the example shown in FIG. 6E, six series of images are shown from a brain MRI. From left to right and top to bottom, the six series shown include: T1 Sagittal, T1 Coronal following administration of gadolinium contrast (indicated by "+Gd"), T1 axial, T1 Axial with contrast, Intermediate Axial, and T2 Axial. In the example shown, the image number within each series is displayed and preceded by "i:", e.g., image 732 is image 21 of the T2 Axial series, displayed as "i:21". Alternatively, the spatial position of each image may be displayed relative to a common coordinate system. In another embodiment, each series of images may be derived from a 3D volume of imaging data, and images displayed may be created using 3D volume rendering techniques, such as multiplanar reformation (MPR), maximum intensity projection (MIP), or volumetric rendering (VR) (as further described below). Each series of images in a virtual array (such as the array shown in diagram 730) may come from the same or different exams of a particular patient, for example, exams obtained at different times and/or with different modalities.

In FIG. 6E, diagram 740 shows three states of mobile computing device 742 (e.g., a smartphone or other mobile computing device) as the user interacts with the array of series of images. In state 742a, a particular image of the virtual image array is displayed, image 732, which is image 21 of the Axial T2 series. As shown, a user may move device 742 laterally left/right and/or up/down, to select another series (or group of series if more than one series is simultaneously displayed as in the example of FIG. 5) within the virtual array of series of images (similar to the selection of images described above with references to FIGS. 5 and 6A-6D).

For example, the user may move the mobile computing device superiorly (e.g., laterally upward), as shown by arrow 743. State 742b represents the updated appearance of the display of the mobile computing device, where according to system and methods described herein, movement of the device is used to select another series, in this example the series represented by image 733, which is superior in the virtual array from image 732. In the example shown, when the series is changed, the particular image displayed from the new series is the one with the same image number. In various embodiments, the image shown from the new series may be an image at a same spatial position as the first image, which may or not have the same image number within the series, particularly if the series are from different exams (for example, exams obtained at different times and/or with different modalities, as described above).

Continuing with the embodiment of FIG. 6E, when a series of images is selected, the user may provide additional input to display other images within the selected series. For example, the user may touch the display of the mobile computing device with his finger and move his finger on the display to select other images within the series. In the example of state 742c, the user has touched a finger to the touchscreen of the mobile device and moved his finger superiorly (e.g., along the direction of arrow 745) to display another image within the selected series, here image 24 of the T1 Axial contrast enhanced series, in comparison to image 21 of the same series shown in state 742b (which was displayed before the user had provided input on the touch screen).

In an embodiment, once a user touches the display of the mobile computing device, motion of the device is ignored so that other series are not inadvertently selected while the user is interacting with the selected series by moving his finger on the screen. In other words, touching the screen may temporarily lock the display to the current series(s) and input from the user via touch of the display (e.g., movement of a finger touch superiorly/inferiorly on the display) allows the user to navigate through images in series by, e.g., incrementing/decrementing the image displayed within the series.

In various other embodiments, other forms of user input may be used to navigate through images within a selected series. For example, the user may move the mobile computing device translationally or rotationally, and/or use voice commands, to select and display other images within the selected image series.

In any of the embodiments described herein, the image display system may be used to view a single large image, such that motion of the mobile computing device may cause panning and/or scrolling around a single large image. Similarly, the system may be used to view/display a series of large images. In an embodiment, when the user views a two-dimensional array of images, or a two-dimensional image, the system zooms in or out on the image in response to motion of the mobile computing system. For example, translational movement the mobile computing device may cause the image to be zoomed in or out, respectively (or vice versa).

Figure 7A:
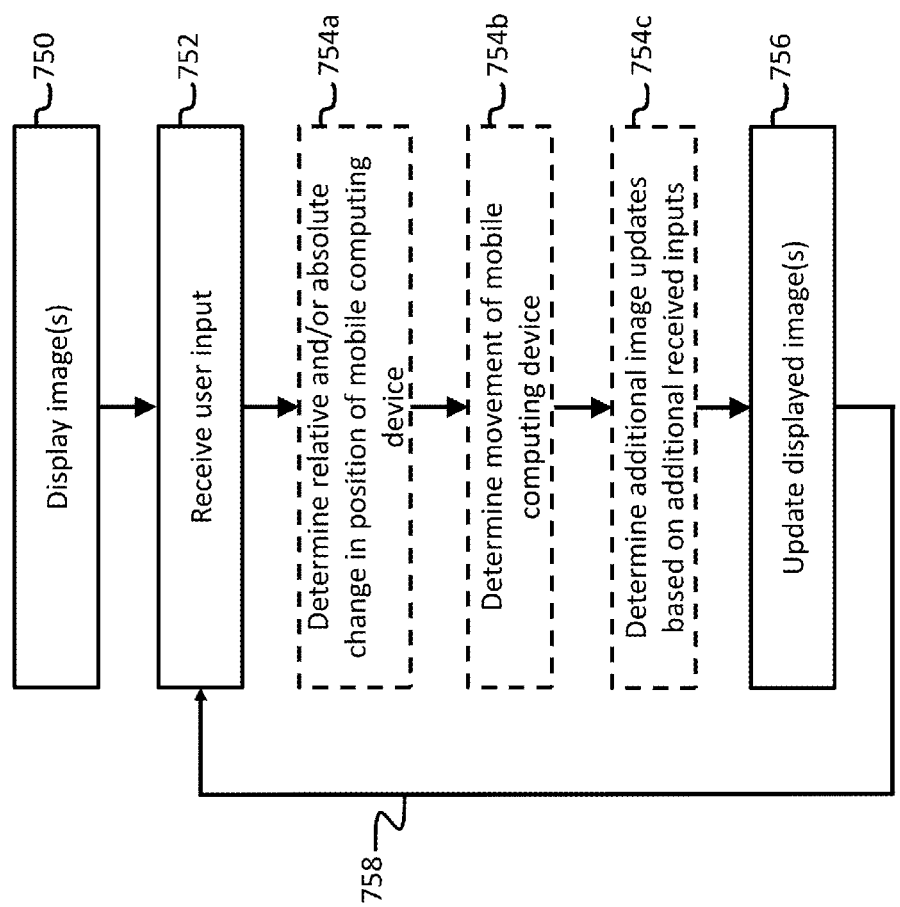
FIG. 7A is a flowchart illustrating an example method of the image display system, according to an embodiment of the present disclosure.

FIG. 7A is a flowchart illustrating an example method of the image display system, according to an embodiment of the present disclosure. The method of FIG. 7A may be performed by the mobile computing device 150 and/or a combination of the mobile computing device 150, the server 120, and/or any other suitable computing device. Depending on the implementation, the system may perform a method having more or fewer blocks than are shown, and/or the blocks may occur in a different order and/or in parallel in order to accomplish the methods and/or processes of the system.

Starting at block 750, the image display system may display an image and/or image array to the user via a display of the mobile computing device. For example, the user may select a particular image/image array to view via the mobile computing device.

At block 752 the mobile computing device may receive one or more inputs from the user. The inputs may include, for example, a movement, change in position, orientation, rotation, and/or any other movement or motion of the mobile computing device. Thus, the user inputs may be provided by the user by simply changing position (including, for example, location and/or orientation) of the mobile device, without providing input via a touchscreen or keyboard, for example. The inputs may optionally further include, for example, one or more touch inputs, button presses, knob turns, and/or the like (to, e.g., select a particular image in a series, to generate a virtual space, etc., as described above). The input may be determined via one or more of the sensors of the mobile computing device, as described above and below in reference to FIG. 1A. In an embodiment the input may be determined by one or more external sensors 124, for example a camera tracking the movement of the mobile computing device or the user. In embodiments in which an absolute position of the mobile computing device is determined (as described below), external sensors and/or, for example, internal GPS sensors may be used.

At optional block 754a the mobile computing device and/or image display system may determine a relative and/or absolute change in the position of the mobile computing device. For example, as illustrated in FIG. 5, the system may determine that the mobile computing device has been moved from a first relative position to a second relative position. Alternatively, the system may determine that the mobile computing device has been moved from a first absolute position to a second absolute position.

Alternative to or in addition to block 752, at optional block 754b the mobile computing device and/or image display system may determine a motion of the mobile computing device. For example, as illustrated in FIG. 6C, the system may determine that the mobile computing device has been moved laterally and/or translationally, but not necessarily that the device has moved a particular distance.

At optional block 754c, the mobile computing device and/or image display system may determine additional image updates based on additional inputs received. For example, and as mentioned above, the user inputs may optionally further include, for example, one or more touch inputs, button presses, knob turns, and/or the like. Such inputs may be used by the system to determine, e.g., that a particular image in a series is being selected (as described above), that images should be virtually located relative to a current position of the mobile computing device (e.g., generate a virtual space, as described below), and/or the like.

Then, at block 756, the mobile computing device and/or system may update the displayed image based on the change in relative and/or absolute position and/or motion of the device, as described above. The displayed image may be updated based on a set of rules. For example, in an embodiment the system may determine, based on a set of rules, that a motion of the mobile computing device a particular distance (for example, a centimeter, an inch, and/or any other distance) is to correspond to an adjustment of the displayed image/image array by a particular amount (for example, display of a different portion of an image, a movement from one image to a neighboring image, or multiple images). Similarly, in an embodiment the system may update the displayed image based on a speed of a movement, a degree of rotation, and/or any other motion. Accordingly, as described above, the movement/change of images displayed on the mobile computing device may be correlated with the motion of the device. Further, the correlated movement of the images may be proportional and/or equal to (and/or any other function of) the motion of the mobile computing device.

In another embodiment, the displayed image may be adjusted (for example, moved) an absolute amount that corresponds to the absolute change in position of the mobile computing device. For example, the system may determine a virtual absolute position and/or size in space of the image (and/or image series). The virtual absolute position of the image/image series may be based on an initial position of the mobile computing device, and/or some other reference. Thereafter, an absolute position of the mobile computing device in relation to the virtual absolute position (and, e.g., virtual absolute size) of the image/image series in space may be used to determine what particular image data is displayed. A few illustrative examples may aid in understanding this embodiment.

1. Single Virtual Image Located at an Absolute Position in Space, with an Absolute Orientation, and Having an Absolute Size.

In this example, suppose the absolute position of the single virtual image is a middle of a room, and the single virtual image has an absolute size. When entering the room without looking though the mobile computing device, the single image would not be visible as it does not exist in the physical world. However, when raising the mobile computing device and virtually viewing the room through the display of the mobile computing device, the single virtual image would appear to exist in the middle of the room, fixed at a particular location and in a particular orientation, and having a particular size. Moving through the room with the mobile computing device, the single virtual image would appear fixed in the particular position, in the particular orientation, and of the particular size. The single virtual image could be viewed up close, or from far away, depending on the location of the mobile computing device (as positioned by the user moving around the room to view different portions of the single virtual image from different angles and at different distances). Further, the single virtual image could be viewed at an angle, or from a back side. The single virtual image would remain fixed in its virtual absolute position, orientation, and size. Only a single two-dimensional image would virtually exist.

2. Single Virtual Two-Dimensional Array of Images at an Absolute Position in Space, with an Absolute Orientation, and Having an Absolute Size.

This example is similar to the single virtual image example above, however the single virtual image is replaced with a single virtual two-dimensional array of images, similar to the array of images 520 shown in FIG. 5. The single virtual array of images may comprise a series of images from a particular exam, for example. This single virtual two-dimensional array of images would be fixed in virtual space in a particular position and orientation, and having a particular size. As with the single image, the user could move about the single virtual two-dimensional array of images using the mobile computing device and view the single virtual two-dimensional array of images from many angles, and from up close or far away. The single virtual two-dimensional array of images would remain fixed in its virtual absolute position and orientation, with its virtual absolute size. Only a single two-dimensional plane of images would virtually exist.

3. Multiple Virtual Images and/or Image Series at Absolute Positions in Space, with Absolute Orientations and Having Absolute Sizes.

The examples above may be extended to multiple virtual images and/or image series in various absolute positions and orientations, and having various absolute sizes. In this example, it may be imagined that the multiple virtual images/image series are located at various places in space within a room. Viewing the room through the mobile computing device, the user may move about and view each of the virtual images/image series. One possible virtual arrangement of the virtual images/image series is on various walls of the room. In this arrangement the user could walk about the room, viewing the various virtual images/image series on the walls through the mobile computing device. In another possible virtual arrangement multiple virtual images may be arrange in a sequential series, one after another, front to back, such as a line of standing dominoes (such as in a domino show) floating in space. In this arrangement, the user may approach a first virtual image in a series and view it though the mobile computing device, and then proceed to move through that first virtual image to a second virtual image, which may then be viewed. The user may similarly move to a side of the sequential series and see all of the series of virtual images lined up, front-to-back, in a line. No matter the movement of the user and the mobile computing device, the multiple virtual images/image series would remain at fixed locations in space, at fixed orientations, and having fixed sizes.

In this third example, the multiple images and/or image series may be arranged in any manner in their fixed positions. For example, multiple image series may be arranged in an array, such as the image series 520 shown in FIG. 5; multiple image series may be arranged in multiple parallel planes; multiple image series may be arranged in multiple non-parallel planes (such as three image planes parallel to three walls of a room); and/or the like.

4. Virtual Three-Dimensional Image Data at an Absolute Position in Space, with an Absolute Orientation, and Having an Absolute Size.

Any of the examples above may be extended to three-dimensional image data. For example, as described below in reference to FIG. 14, a virtual three dimensional volume of image data may be fixed at a particular location, be fixed in a particular orientation, and have a particular size, in virtual space. Accordingly, as with the two-dimensional examples described above, moving around and through the room with the mobile computing device, the virtual three-dimensional volume would appear fixed in the particular position and in the particular orientation. This and the examples above may similarly be extended to multiple virtual three-dimensional volumes and/or combinations of two- and three-dimensional image data located at respective particular positions and orientations, and having particular sizes, in virtual space.

Accordingly, in the various illustrative examples above, the mobile computing device may act as a kind of window into a virtual world in which the image/image series is in a particular position that may be viewed through the display of the mobile computing device. In this embodiment, when the image data is two-dimensional (for example, in the case of a two-dimensional image and/or image series), moving the mobile computing device closer or further from a plane of the image/image series (e.g., moving the device translationally) may have the effect of showing the image/image series being closer or further away (e.g., by adjusting zoom level of the image/image series) as the virtual position and size of the image/image series is fixed. Further, this may mean that the display of the device may be obliquely oriented relative to any particular virtual image. While in some embodiments such obliquely oriented images are displayed on the mobile device with a 3D perspective that would result from such oblique orientation, in some instances such image distortion may be undesirable.

Accordingly, in some embodiments, a position of the mobile device may be used to choose images to display, but the images displayed on the mobile device may be displayed in an original undistorted manner, as the user would see if they were viewing the images straight on, without any obliquity. Accordingly, in these embodiments, any angle of the mobile computing device relative to a virtual image may be decoupled from how the image is displayed to the user. For example, various images and/or image series may be mapped to particular locations in virtual space, but rather than the images appearing to be permanently located in particular orientations and/or at particular sizes, when the mobile computing device is moved to each respective particular location in space the image/image series is displayed on the display at a size relative to the display. This is illustrated in FIG. 5 (described above) where mobile computing device 501 in position 505*c* is angled obliquely with respect to virtual image array 520, but points to virtual images 529*a* and 530*a*, and therefore those two images are selected and displayed on the device. In this way the device can be translated and rotated to point to images for selection, but the images displayed on the mobile device are the original images, e.g., the images are not distorted as a result of viewing them obliquely (as they may be, for example, if the user were viewing a physical computer display containing image array 520).

Thus, for example, each of a series of images may be mapped to particular locations in space that form a line. This may be conceptualized as a linear trail of virtual bread crumbs suspended in a particular location in space. As the mobile computing device is moved from one breadcrumb to the next, regardless of the particular orientation of the mobile computing device, the image corresponding to that location in space is fully displayed on the display. In some instances, the locations may be linear, while in others the locations may be organized in any way (as described above). The locations may be determined relative to an initial position of the mobile computing device, or based on any other frame of reference. In some embodiments, there may be a conceptual "zone" surrounding each of the locations in space such that an image corresponding to a location closest to the mobile computing device, while the mobile computing device is also within the "zone" of that location, is displayed. In some embodiments, a closest location to the mobile computing device is used to determine an image to display.

In one embodiment, an initial view of images may include the 3D perspective, so that the user perceives that he is in a 3D virtual space, but the user may then provide an input to the mobile computing device (for example, using a virtual or real button, by touching the screen, or a voice command) to cause display of images in an undistorted manner.

As mentioned above, in various embodiments the absolute virtual positions, sizes, etc., of images may be determined relative to a position and/or orientation of the mobile computing device. For example, while in some embodiments the virtual spaces described above may correspond to actual physical locations (e.g., a particular physical room), in other embodiments the system enables a user to create a virtual space (e.g., a virtual room) on demand, wherever the user is located with the mobile computing device. Generation of a virtual space may be initiated, for example, but user input selecting a button on the mobile computing device. This is illustrated below in reference to FIG. 7B.

Figure 7B:
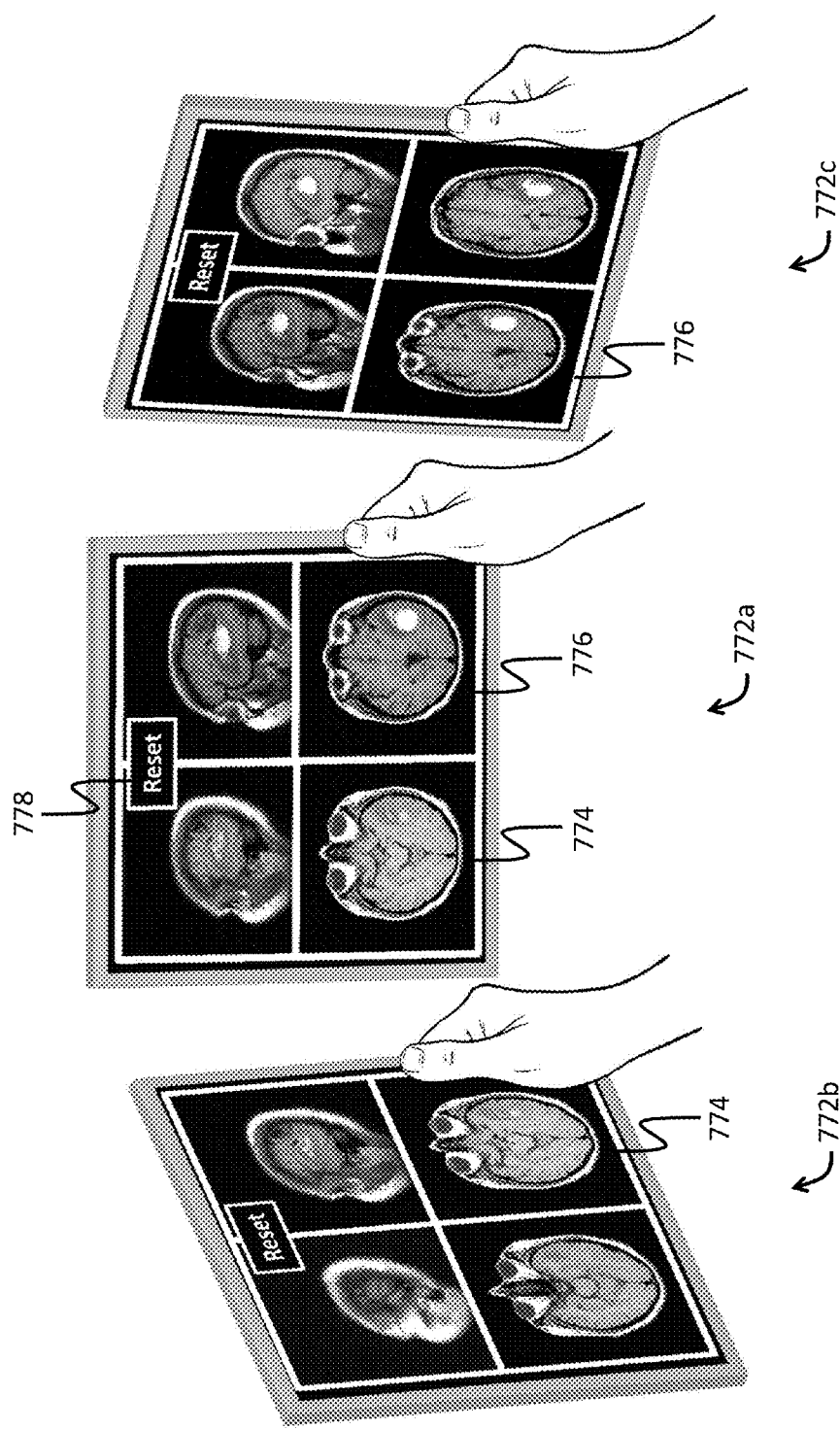
FIG. 7B illustrates example user interactions with a mobile computing device of the image display system, according to an embodiment of the present disclosure.

FIG. 7B illustrates example user interactions with a mobile computing device of the image display system in which a user may designate a virtual space on-demand, according to an embodiment of the present disclosure. As shown, the user may hold the mobile computing device in an initial position 772a. The user interface of the device may include a "Reset" button 778 that the user may use to initiate a virtual space. Initiation of a virtual space may include designation of an initial virtual position of image data (e.g., images and/or series of images) relative to a position of the mobile computing device when the "Reset" button 778 is selected. For example, having moved the mobile computing device to the position 772a shown, and having selected to view particular imaging data comprising an array of images similar to the array of images 520 of FIG. 5, the user may select to "Reset" button 778 to designate the current position 772a as an initial position. Thereafter, positions of imaging data (in this example, the virtual location of the array of images) may be based on the designated initial position, and movement of the mobile computing device from that initial position is used to determine changes in display image data (in this example, other images of the array of images). Thus, as shown in FIG. 7B, while images 774 and 776 are shown at position 772a, when the user moves the mobile computing device to position 772b or 772c (e.g., via angular motion), the displayed images of the image array are correspondingly updated on the display relative to the initial position.

Similarly, the user may, on-demand, initiate a three-dimensional virtual space (such as the virtual rooms described in reference to the four examples above) at any particular location by similar input to the mobile computing device.

While the description above describes on-demand virtual spaces being initiated by selection of a "Reset" button, any other input from the user may be used to designate an initial position.

In various embodiments, initial positions of imaging data (for example, in response to selection of the "Reset" button) may be determined based on, e.g., user preferences that may be preset and may be associated with particular users, groups of users, and/or the like, of the mobile computing device. Accordingly, the system may include user interfaces to enable a user to specify, store, retrieve, and utilize user preferences for how virtual spaces are configured when created. Such user preferences may indicated, for example, a size of a virtual room, virtual arrangement of images and image series within a virtual room, aspects of how interaction with images is to occur (for example, as described in reference to any of the four examples above), and/or the like. For example, in the instance of a two-dimensional image array, the user preferences may specify arrangement of the images in the array, and/or that an initial position of the view of the array is to be at a center of the image array. In another example, in the instance of two-dimensional images located at various placed in a virtual room, the user preferences may specify positions and sizes of the various images. Such user preferences may further specify types of motion that may be used to move among images (e.g., angular motion, translational motion, lateral motion, rotational motion, and/or combination of the above). In another example, such user preferences may further specify whether displayed images to be shown with a 3D perspective (e.g., obliquely, as described above) or without any distortion. Such preferences may further be based on types of imaging data, and/or types of exams from which the imaging data is obtained.

Returning to the flowchart of FIG. 7A, as indicated by arrow 758, the system may then receive additional user inputs and proceed again as described above. In many of the embodiments and examples described above, virtual images and/or image arrays are illustrated and/or described as being flat.

In some embodiments, the virtual images/image arrays may be curved such that, for example, all images point toward the user when viewed through the mobile computing device, eliminating distortion related to viewing images obliquely.

In an embodiment, lateral and translational motion may be ignored and device rotational motion (and/or an absolute angle of the device) alone may be used to select images. For example, images within a virtual image array may be positioned along a curved 3D surface (e.g., a portion of a hemisphere) such that each image is angled so that its surface faces the user. In this example, angulation of the device up-down and left-right (e.g., rotational motion) may be used to select images for viewing from the curved image array and each image may be presented without the distortion that would result from a flat image being viewed obliquely.

Display of and Interaction with, Three-Dimensional Images/Data

In various types of medical imaging a three-dimensional (3D) volume of data may be acquired via, for example, Magnetic Resonance Imaging (MRI), Computed Tomography (CT), Positron Emission Tomography (PET), ultrasound, and/or the like. Existing display technologies for volume rendering include, for example, multiplanar reformation (MPR), maximum intensity projection (MIP), 3D volume rendering, and 3D surface rendering. Such volume rendering technologies allow users to display 3D imaging volumes on, for example, an electronic display as a virtual three-dimensional volume and/or a portion of a virtual three-dimensional volume. For example, with multiplanar reformatting, a user may view arbitrary planes of information from within the 3D volume of data. With volume rendering, the user may view 3D views of the information. In another example, two-dimensional images, or a series of two-dimensional images may be composed into a virtual three-dimensional volume viewable by a user.

In order for a user to interactively explore rendered information from a 3D dataset using 3D display techniques, three things may be needed:
1. Rendering software that creates an image such as a 3D volume rendering or MPR reconstructed image based on the 3D volume of data and input parameters from the user, for example, 3D orientation information for rendering of a 3D volume or rendered image, or a location of the plane (or slice) and slice thickness that the user desires to view for an MPR reconstruction.
2. An input device that the user may use to provide input parameters to the rendering software.
3. A display device to display the rendered information to the user, for example, a desktop computer monitor or the computer display integrated into a mobile computing device.

Previously users may have been limited in the ways in which they could view and interact with such virtual three-dimensional volumes. For example, a user may be limited to use of a mouse and keyboard as inputs, while the three-dimensional volume is displayed on a monitor of desktop computer.

Advantageously, the present disclosure describes methods and systems that may enable a user to intuitively, efficiently, and interactively view and explore 3D information. According to various embodiments, a user of the image display system may interact with a virtual three-dimensional volume or model, or a series of two-dimensional images composed in a virtual three-dimensional space, via a mobile computing device. Motion and/or absolute location of the mobile computing device in two- or three-dimensional space may cause display of the three-dimensional volume and/or slices of the three-dimensional volume to be updated on the mobile computing device. For example, translational motion of the mobile computing device may cause a corresponding virtual movement toward, away from, and/or through (for example through slices of) a displayed virtual three-dimensional volume. Similarly, rotational motion of the mobile computing device may cause a corresponding virtual rotation of the displayed virtual three-dimensional volume. Further, other types of motion (including any combination of lateral, translational, and/or rotational motion) of the mobile computing device may cause corresponding portions of three-dimensional imaging data to be displayed. Accordingly, using the image display system a user may efficiently view and/or interact with a three-dimensional volume displayed via a mobile computing device.

FIGS. 8-9, 10A-10B, and 11-14 illustrate example user interactions with virtual three-dimensional volumes (or series of two-dimensional images composed in virtual three-dimensional space) via a mobile computing device of the image display system, according to various embodiments of the present disclosure.

Figure 8:
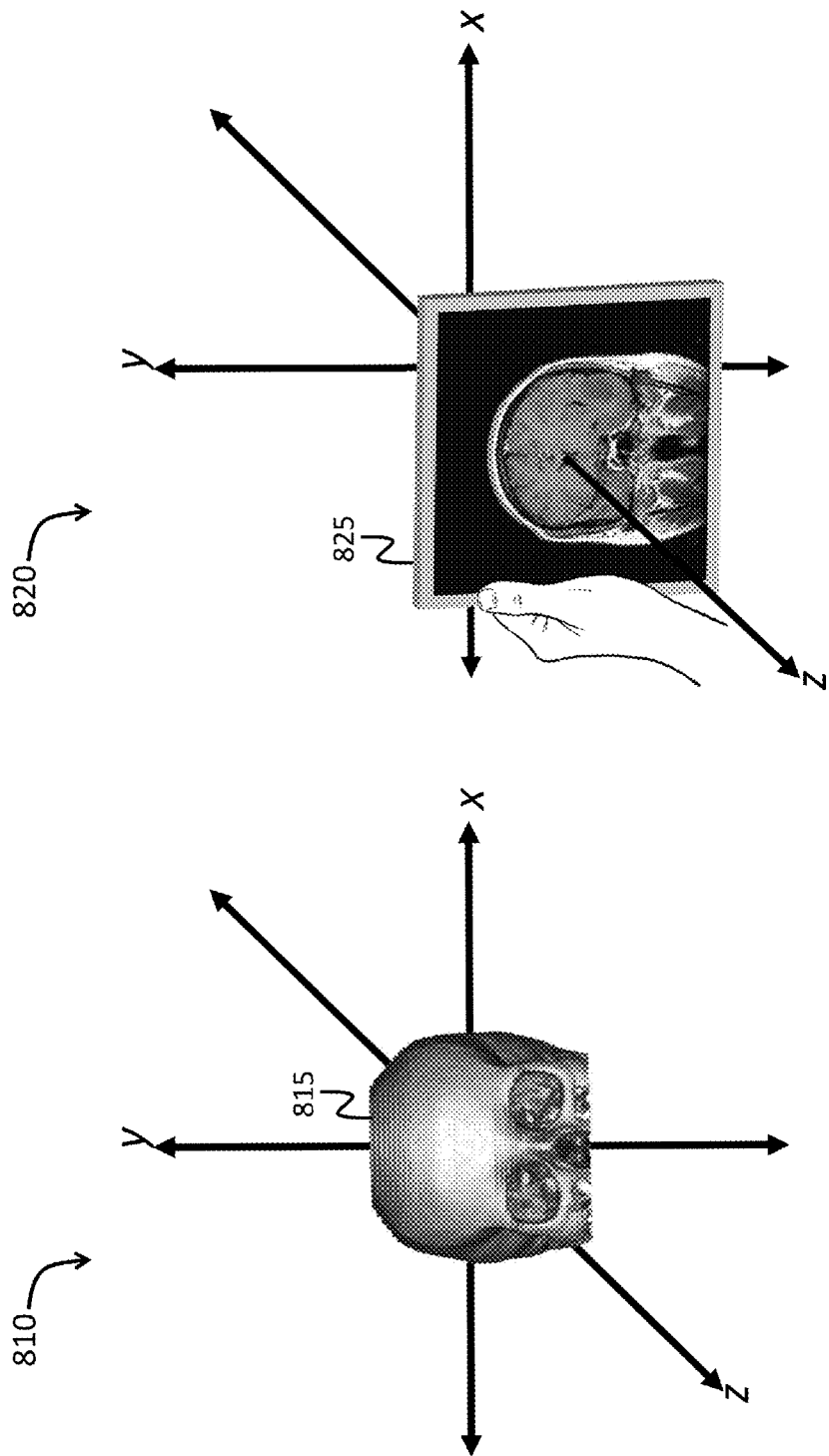

Referring to FIG. 8, view 810 illustrates an example virtual 3D data volume 815 (for example, constructed from MRI or CT imaging data) in a virtual three-dimensional space. The virtual three-dimensional volume may be rendered, for example, by a computing device such as the mobile computing device 150 and/or the server 120. The three-dimensional rendering may be based on three-dimensional or two-dimensional data obtained via any of the methods disclosed herein and stored, for example, in the image storage 122.

View 820 of FIG. 8 illustrates a mobile computing device 825 (in this example, a tablet, although any other suitable mobile computing device may be used) including an electronic display and one or more sensors that may be used as inputs to provide input to rendering software (for example, movements, location changes, orientation changes, and/or rotations, as described above and below). In various embodiments, any or a combination of the position, location, motion, and/or orientation of the mobile computing device may be used to determine an imaging plane to display within the 3D volume (in this example, a coronal plane of a brain MRI).

In an embodiment, an imaging plane/slice to be displayed may be calculated from the 3D imaging volume and/or 3D imaging data using, for example, MPR. In another embodiment, input from the user may be used to determine which image to display from a series of 2D images that were previously obtained or pre-calculated, for example, a 2D coronal series from a brain MRI.

In various embodiments, tracking of a position (including, for example, location, motion, and/or orientation) of the mobile computing device may be performed by components or devices external to the mobile computing device itself. For example, an external camera or other sensor may be used to track the position of the mobile computing device and/or user using the mobile computing device.

FIG. 9 illustrates an example mobile computing device 825 in three translational positions: 825a, 825b, and 825c. As the user physically moves the device translationally from an anterior position (825a) to a posterior position (825c), images are displayed on the device corresponding to anterior-to-posterior locations within an imaging volume. For example, in FIG. 9 moving the mobile computing device translationally from front to back causes display of images from a front to a back of an imaged brain. While only three images are shown in the example illustrated, any number of images might be shown along the translational motion. Additionally, the image display system may employ one or more rules that are executed by, for example, the rules engine 163 (as described above and below) that may translate an amount of movement of the device into a corresponding movement through the imaging volume or series of images. Similar to the embodiments described above, the movement/change of images displayed on the mobile computing device may be correlated with the movements of the device. For example, a movement of the mobile computing device a particular distance forward (e.g., translationally) may cause a correlated translation or movement of the displayed images/slices forward into the 3D volume. In an embodiment, the correlated movement of the images may be proportional and/or equal to the motion of the mobile computing device.

In an embodiment, displayed images (such as the images displaying in FIG. 9) are calculated, for example, from a 3D imaging volume using MPR, Maximum Intensity Projection (MIP), or another technique. In another embodiment, images are chosen for display from a series of images or pre-calculated 2D images.

Figure 10A:
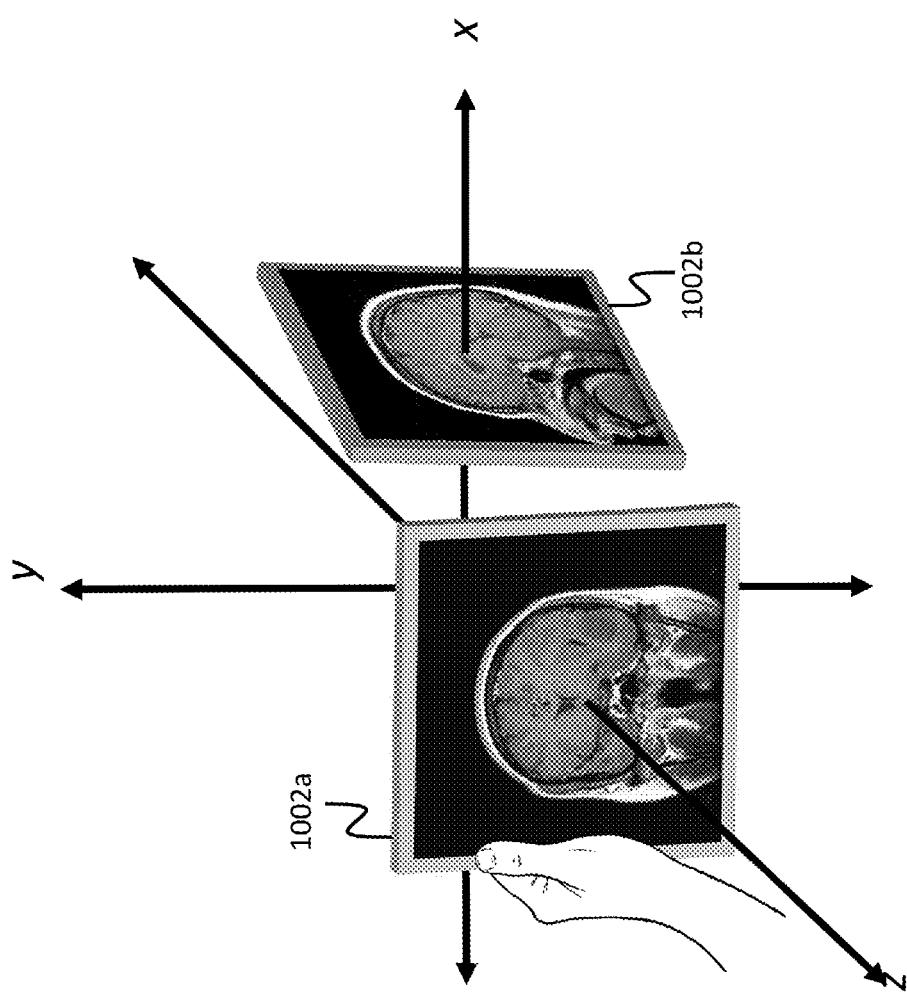

FIG. 10A illustrates how, according to an embodiment, the user may not only move the device translationally, but may also move the device rotationally to visualize imaging information along other axes. As shown, a mobile computing device in a first position and/or orientation 1002a displays a coronal brain MRI image, and in a second position and/or orientation 1002b, a sagittal brain MRI image. Accordingly, from the perspective of the user of the mobile computing device, rotational movement of the mobile computing device may cause a corresponding virtual rotation of displayed images of the virtual three-dimensional volume.

Figure 10B:
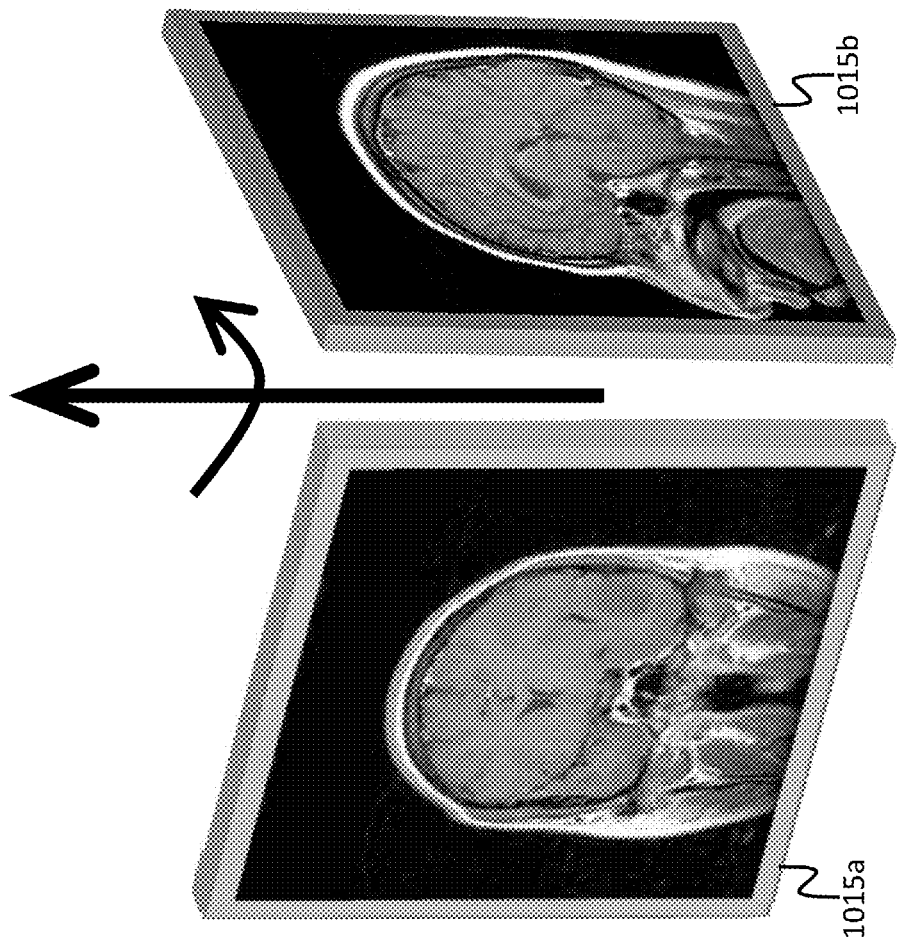

FIG. 10B illustrates another example, similar to FIG. 10A, of how, according to an embodiment, physically changing a position of the mobile computing device from one position to another may change a plane of the image that is automatically displayed. For example, in position 1015*a* a coronal brain MRI image is displayed, and, in response to changing to a different position and/or orientation 1015*b* that is perpendicular to the plane of 1015*a* (e.g., rotational motion), an image in the corresponding perpendicular plane is displayed, in this example a sagittal brain MRI image. As described above, the movement/change of images displayed on the mobile computing device may be correlated with the motion of the device.

In an embodiment, rotational motion of the mobile computing device (such as in FIGS. 10A-10B) may be used to choose among various series in an exam. For example, rotational motion may be used to select images from coronal series or sagittal series, similar to the description above. In some scenarios, more than one series of images may be available for a given orientation. For example, axial CT scans may be available for two different exam dates. In another example, a single exam may include multiple series with the same orientation, for example a brain MRI could include axial T1, FLAIR and T2 series before contrast administration and an axial T1 series after contrast administration. In an embodiment, if more than one series is available for a given position/orientation of the mobile computing device, then other user input may be used to choose from among the series of the chosen orientation. For example, such other user input may include touch input on the device screen, pressing a button, voice input, and/or motion of the device (for example, lateral and/or translational motion). The system may also provide a user interface by which the user is notified that multiple series are available for a given orientation and/or view, and provide functionality such that the user may select on the multiple series.

While the description of FIGS. 10A-10B above involves rotational motion about a particular axis, similar to the description below in reference to FIG. 12, rotational motion around any arbitrary point may be used to cause a corresponding virtual rotation of displayed images of the virtual three-dimensional volume.

Figure 11:
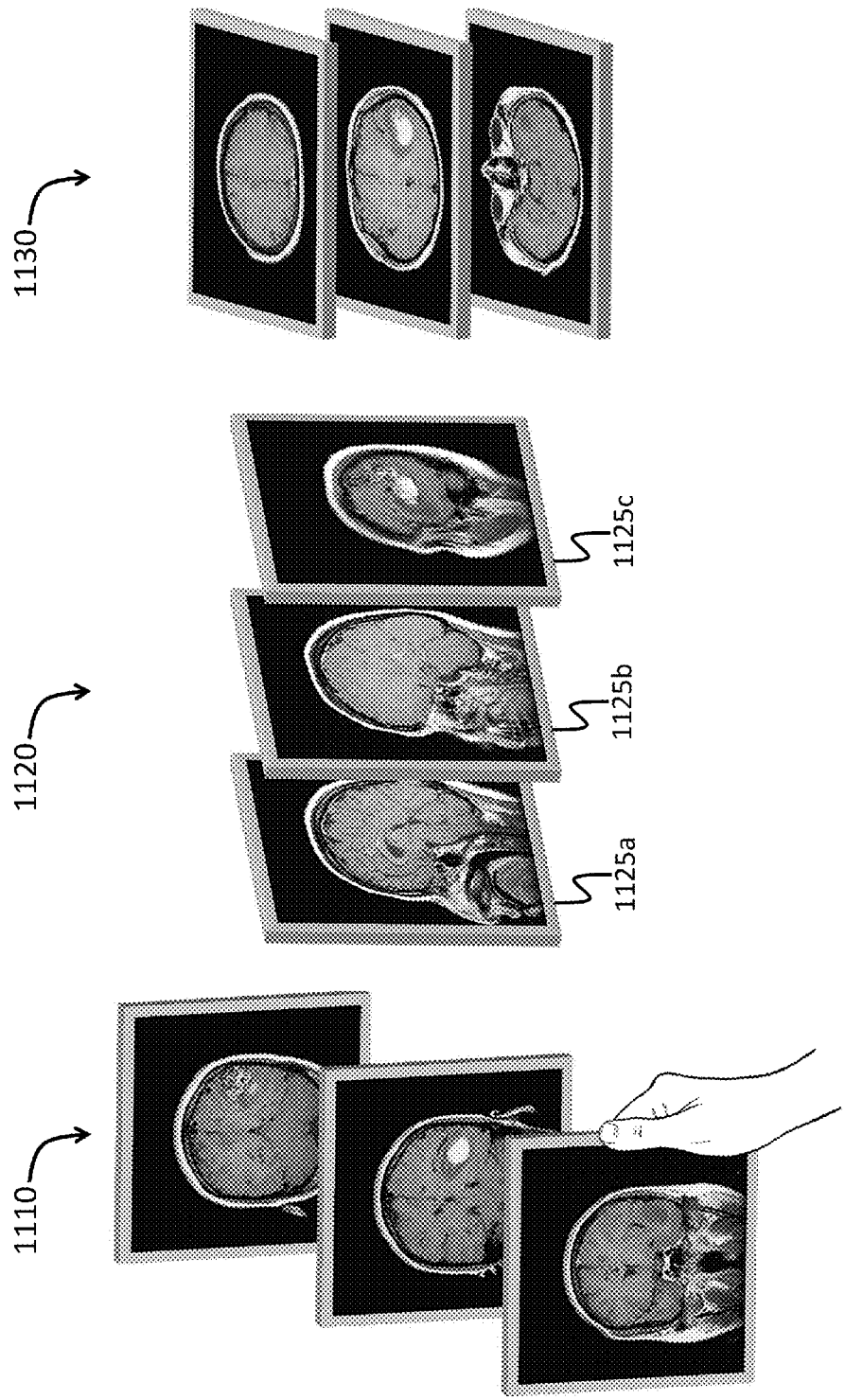

FIG. 11 illustrates how, according to an embodiment, a user may navigate through imaging information by changing the position and/or orientation of the mobile computing device. For example, views 1110, 1120 and 1130 illustrate a mobile computing device in different positions and/or orientations displaying images of a brain MRI in coronal, sagittal, and axial orientations, respectively. As shown, in each of the three orientations 1110, 1120 and 1130, as the user moves the mobile computing device translationally, appropriate planes and/or slices of the three-dimensional volume (or series of two-dimensional images) are displayed (as described above in reference to FIG. 9). As mentioned above, in some embodiments that user may select a particular imaging information (for example, series of images and/or rendered 3D imaging data) to view when multiple imaging information is available for a given position/orientation of the mobile computing device.

Figure 12:
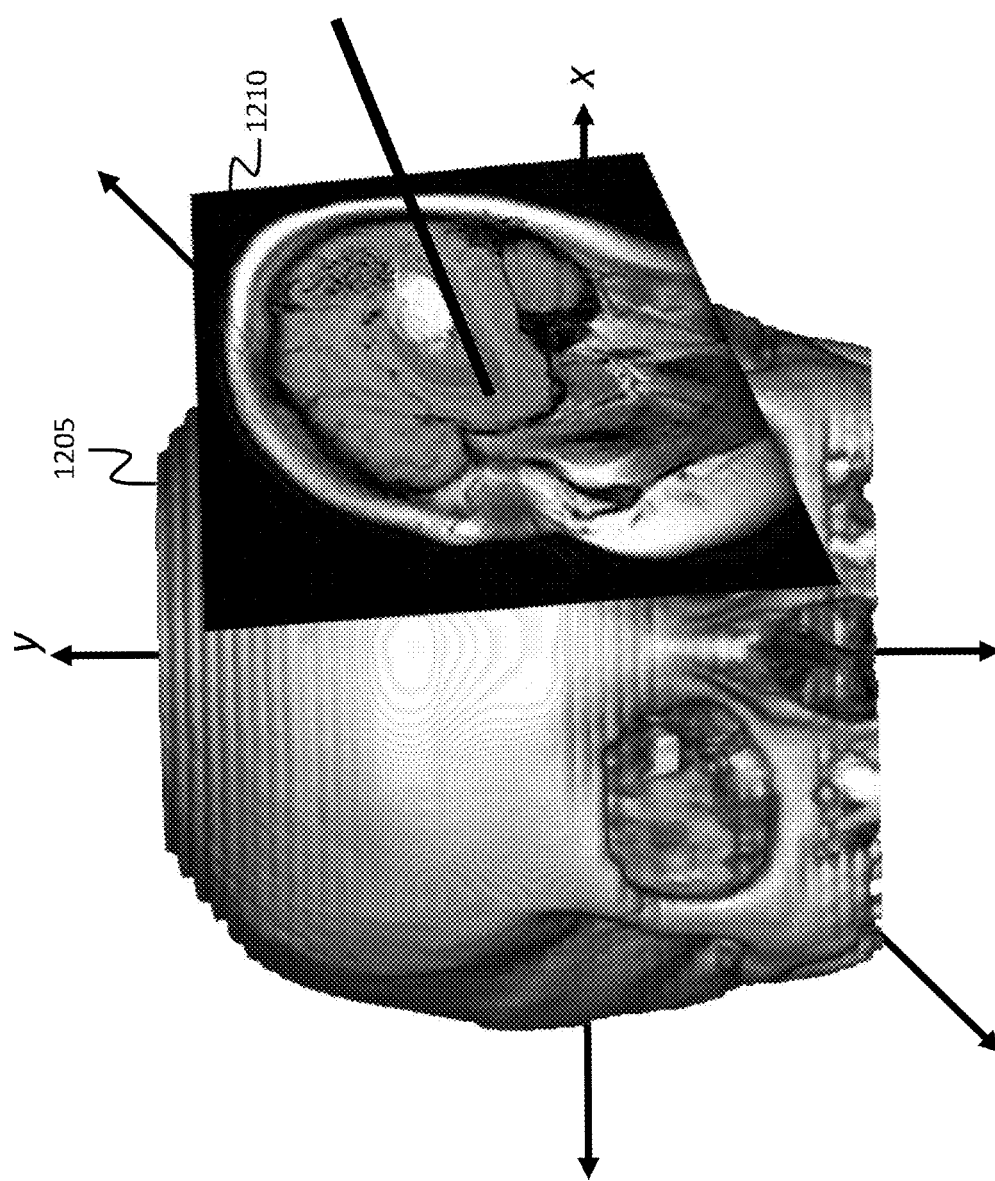

FIG. 12 illustrates an example of display of visual information along an arbitrary plane, here an oblique sagittal plane. While FIGS. 9, 10A-10B, and 11 illustrate display of image information along three perpendicular planes, the systems and methods described herein may allow navigation through, and display of, information in any arbitrary position and/or orientation. In FIG. 12, 1205 represents 3D data that may be displayed using 3D rendering software such as volume rendering, MPR, or MIP. A position and orientation of mobile computing device 1210 may be used as input to the rendering software. Based on the position of mobile computing device 1210, 3D rendering (MPR in the example of image 1210) may be performed and rendered images may be displayed on the device. As described above and throughout, the same methods may be applied to display of two-dimensional image series having arbitrary imaging planes. In an embodiment, the system may determine a closest available image to a particular place of the mobile computing device and display that determined image.

Figure 13:
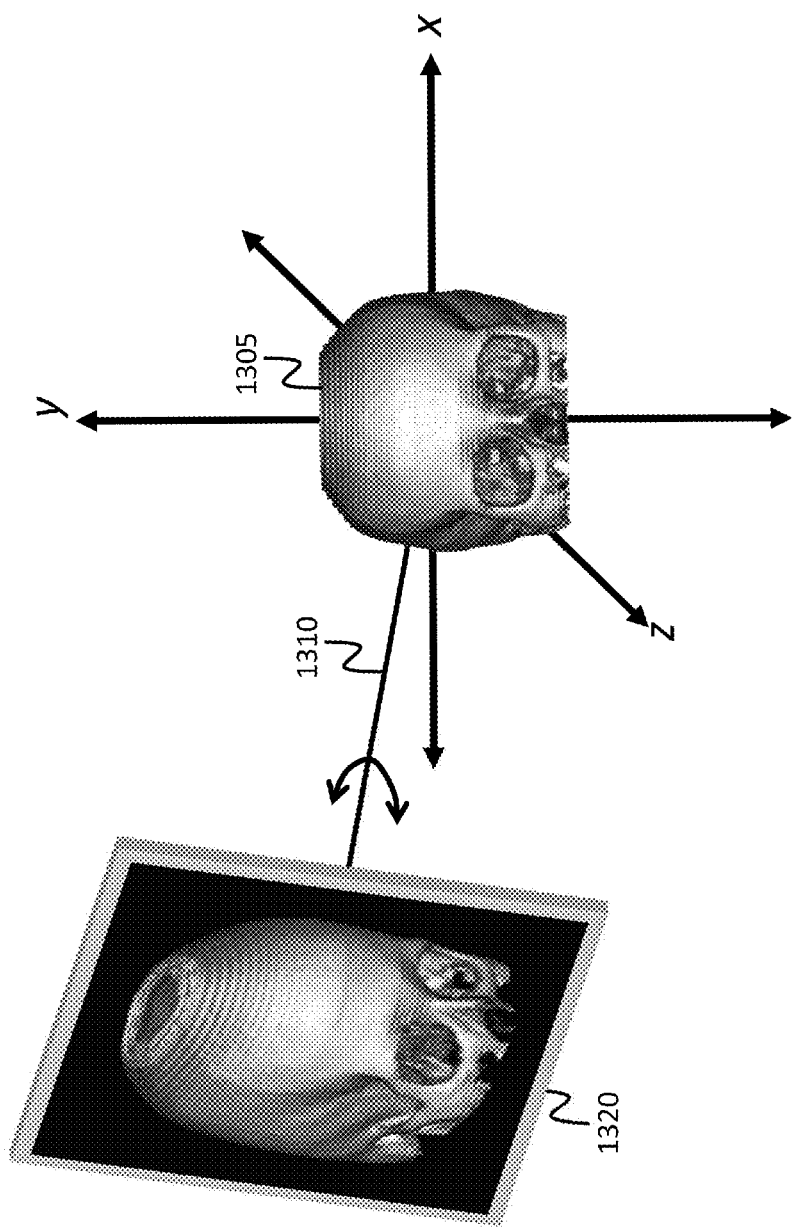

FIG. 13 illustrates an example of a user interacting with a 3D volume of information 1305, for example, a volumetric imaging of a patient's brain using MRI, CT, or PET. Various 3D volumetric display techniques may be used to render images to allow the user to visualize the information. As described above, the user may provide input to a mobile computing device 1320 that determines how the information is to be rendered and displayed by changing the position and/or orientation of the mobile computing device. In the example, mobile computing device 1320 displays an example 3D volumetric image calculated from the 3D volume of information 1305 in a plane perpendicular to arbitrary axis 1310.

Using system and methods described herein, a position, orientation, and/or motion of mobile computing device 1320 may be used as input parameters to determine the view displayed. In the example shown, mobile computing device 1320 is perpendicular to an arbitrary axis 1310 so that the view that is rendered for display is from that perspective. The user may move the mobile computing device to other positions and orientations to view the data from a different orientation and/or distance. Accordingly, in various embodiments the position, orientation, location, and/or movement of the mobile device may be used to determine the position and orientation of a virtual camera viewing the 3D data volume. In various embodiments, external sensors, such as cameras, may be used to track the position, orientation, and/or movement of the user. Further, such position tracking information may be used to determine the position and orientation of a virtual camera viewing the 3D data volume.

FIG. 14 further illustrates how, according to an embodiment, the user may change the position of mobile computing device 1410 to view 3D data volume 1405 from different orientations 1410*a*, 1410*b*, and 1410*c*. In all of the embodiments described above, the movement/change of images displayed on the mobile computing device may be correlated with the motion of the device. Further, the correlated movement of the images may be proportional to the motion of the mobile computing device.

In various of the embodiments described above, 3D imaging data may be pre-rendered by, for example, the server 120. Thereafter, the pre-rendered data may be displayed on the computing device as described above such that the portion of the pre-rendered data displayed may be updated in response to movements of the computing device.

In various of the embodiments described above, a user may provide an input to the mobile computing device so as to designate a virtual position of the 3D imaging data. For example, similar to the functionality descried above in reference to FIG. 7B, the user may select a "Reset" button to designate an initial virtual position of a 3D data volume to be displayed, the initial position being relative to the mobile computing device at the time the "Reset" button is selected. In various embodiments, as described above, initial positions of imaging data may be determined based on, e.g., user preferences that may be preset and may be associated with particular users, groups of users, and/or the like, of the mobile computing device.

FIG. 15 is a flowchart illustrating an example method of the image display system, according to an embodiment of the present disclosure. The method of FIG. 15 may be performed by the mobile computing device 150 and/or a combination of the mobile computing device 150, the server 120, and/or any other suitable computing device. Depending on the implementation, the system may perform methods having more or fewer blocks than are shown, and/or the blocks may occur in a different order and/or in parallel in order to accomplish the methods and/or processes of the system.

Starting at block 1552 three-dimensional data and/or a three-dimensional volume may be displayed on a mobile computing device (such as the mobile computing device 150). The three-dimensional data may be rendered and/or may be composed of a series (or multiple series) of two-dimensional images.

At block 1554 one or more user inputs is received at the mobile computing device. As described above, the user inputs may include any of a change of position, orientation, and/or location of the mobile computing device and/or user, and/or movement of the mobile computing device and/or user. The inputs may optionally further include, for example, one or more touch inputs, button presses, knob turns, and/or the like (to, e.g., select a particular image in a series, as described above). The input may be determined via one or more of the sensors of the mobile computing device, as described above and below in reference to FIG. 1A. In an embodiment the input may be determined by one or more external sensors, for example a camera tracking the motion of the mobile computing device and/or user.

Optional blocks 1556, 1558, and 1559 of FIG. 15 are similar to optional blocks 754a, 754b, and 754c of FIG. 7A. For example, based on the user input, the system and/or mobile computing device may determine one or more of: a relative change in position of the mobile computing device and/or user, a change in an absolute position of the mobile computing device and/or user, a movement of the mobile computing device and/or user, a rotation of the mobile computing device and/or user, a change in orientation of the mobile computing device and/or user, and/or the like. Further, the mobile computing device and/or image display system may determine additional image updates based on additional inputs received, such as one or more touch inputs, button presses, knob turns, other movements, and/or the like. Such optional additional inputs may be used by the system to determine, e.g., a further adjustment to a displayed image (such as a fine adjustment on an image plane of an image and/or a slice thickness of an image), that image data is to be virtually located relative to a current position of the mobile computing device (e.g., generate a virtual space, as described above), and/or the like.

At blocks 1560 and/or 1562 of FIG. 15 the system and/or mobile computing device may determine and/or calculate an image plane and/or slice of the three-dimensional volume to display. Alternatively, the system may determine a particular view of the three-dimensional volume using 3D volume rendering or 3D surface rendering (and/or any other method of volume rendering as described herein). Further, in an embodiment the system may determine a particular image of one or more series of two-dimensional images that is closest to the current view. As described above, the particular image/slice/plane/view shown may be determined based on a set of rules. For example, in an embodiment the system may determine, based on a set of rules, that a movement of the mobile computing device a particular distance (for example, a centimeter, and inch, and/or any other distance) is to correspond to an adjustment of the displayed image/volume by a particular amount (for example, a movement from one image plane to a neighboring image plane). Accordingly, as described above, the movement/change of images displayed on the mobile computing device may be correlated with the motion of the device. Further, the correlated movement of the images may be proportional and/or equal to the motion of the mobile computing device. Additionally, in an embodiment the system may update the images based on a speed of a movement, a degree of rotation, and/or any other motion.

Additionally, in another embodiment as described above, the displayed image/slice/plane/view may be adjusted by an absolute amount that corresponds to the absolute change in position of the mobile computing device. For example, the system may determine a virtual absolute position in space of the three-dimensional volume. The virtual absolute position of the three-dimensional volume may be based on an initial position of the mobile computing device, and/or some other reference. Thereafter, an absolute position of the mobile computing device in relation to the virtual absolute position of the three-dimensional volume in space may be used to determine what particular image data is displayed. For example, if the mobile computing device is moved through the virtual absolute position of the three-dimensional volume, slices corresponding to the position (including the location and/or orientation) of the mobile computing device are displayed. Accordingly, the mobile computing device may act as a kind of window into a virtual world in which the three-dimensional volume is in a particular position that may be viewed (both external to the three-dimensional volume and internal to the three-dimensional volume) through the display of the mobile computing device.

The determined and/or calculated image or view (as described above) is then displayed to the user. As indicated by arrow 1564, the system may then receive additional user inputs and proceed again as described above.

Example Computing Systems

Referring again to FIG. 1A, various configurations of the computing system and network environment 100 may be used to implement and/or accomplish the systems and methods disclosed herein. For example, the mobile computing device 150 may be configured to display and/or enable a user to view and/or interact with various types of information including two-dimensional images, three-dimensional volumes, and/or patient information, as described above.

As described above, the mobile computing device 150 may take various forms. In various embodiments, the mobile computing device 150 may be an information display computing device, a computer workstation, a desktop computer, a laptop computer, a smartphone, a tablet computer, a wearable computer (for example, a head-mounted computer and/or a computer in communication with a head-mounted display), a smartwatch, a mobile computer, a cell phone, a personal digital assistant, a gaming system, a kiosk, an audio player, and/or any other device that utilizes a graphical user interface, such as office equipment, automobiles, airplane cockpits, household appliances, information and other kiosks, ticketing kiosks, vending machines, industrial equipment, and/or a television, for example. In an embodiment the mobile computing device 150 comprises one or more computing devices in communication with one another.

The mobile computing device 150 may include various components including, for example, one or more processors 152, memory and/or data storage 153 (including one or more software modules 151 and/or a rules engine 163 (which may itself comprise a software module)), an operating system 154, a display 155, one or more input devices 156, one or more interfaces 157, an audio input/output 158, and/or one or more position sensors 161 (including, for example, zero or more motion sensors 159, zero or more orientation sensors 160, and/or zero or more location sensors 162). Each of the components of the mobile computing device 150 may be connected and/or in communication with each other using, for example, a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of mobile computing device 150 (as described above and below) may be combined into fewer components and modules or further separated into additional components and modules.

In various embodiments the software modules 151 may provide functionality as described above with reference to the various figures. For example, modules 151 of the computing device 150 may include image display modules, motion detection/determination modules, orientation detection/determination modules, position detection/determination modules, location detection/determination modules, patient information display modules, rules engine modules (for example, rules engine 163), and/or the like. For example, each of the motion, orientation, position, and/or location detection/determination modules may determine user movements of the mobile computing device 150 such that the user may interact with two-dimensional and three-dimensional images and/or volumes, as described above. Further, the image display modules may display images on the display 155 in response to movements of the mobile computing device 150. The rules engine 163 may operate in conjunction with the other modules to perform various functionality of the display systems described above. For example, the rules engine 163 may determine that a particular type of movement of the mobile computing device 150 is to be translated into a particular adjustment of a displayed image. Such a determination may be based on, for example, an image type.

As described below, the software modules 151 may include various software instructions, code, logic instructions, and/or the like that may be executed by the one or more processors 152 to accomplish the functionality described above. In other embodiments, software modules 151 may reside on another computing device, such as a web server or other server (for example, server 120) or other server, and a user may directly interact with a second computing device that is connected to the other computing device via a computer network.

The computing device 150 may run an off-the-shelf operating system 154 such as a Windows, Linux, MacOS, Android, or iOS. The computing device 150 may also run a more specialized operating system which may be designed for the specific tasks performed by the computing device 150.

The mobile computing device 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Objective-C, Swift, JavaScript, ActionScript, Visual Basic, HTML, Lua, C, C++, or C#. While "modules" are generally discussed herein with reference to software, any modules may alternatively be represented in hardware or firmware. In various embodiments, the modules described herein refer to logical modules that may be combined with other modules or divided into submodules despite their physical organization or storage.

The mobile computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

Display devices 155 may include a video display, such as one or more high-resolution computer monitors, or a display device integrated into or attached to a laptop computer, handheld computer, smartphone, smartwatch, wearable computer, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers. As described above, images and other information may be displayed to the user via the display devices 155 such that the user may efficiently view and interact with such images and information.

The mobile computing device 150 may also include or be interfaced to one or more input devices 156 which receive input from users, such as a keyboard, trackball, mouse, 3D mouse, dial and/or knob (for example, a smartwatch crown), drawing tablet, joystick, game controller, touch sensitive surface (for example, capacitive or resistive touch screen), touchpad, accelerometer, video camera and/or microphone.

The mobile computing device 150 may also include one or more interfaces 157 which allow information exchange between mobile computing device 150 and other computers and input/output devices using systems such as Ethernet, Wi-Fi, Bluetooth, as well as other wired and wireless data communications techniques.

The mobile computing device 150 may include the audio input/output 158 for receiving, for example, audio commands or other input from the user. The audio system may also provide audio output to provide audio information to a user, for example via a speaker or headset. As described above, various sensors of the mobile computing device 150 may include, for example, gyroscopes, accelerometers, cameras, Global Positioning System (GPS) transceivers and devices, near field communication (NFC) technology devices, Radio Frequency Identification (RFID) device, systems and devices utilizing WiFi, systems and devices utilizing Bluetooth such as iBeacons, and/or the like. The various sensors may provide input/data to the mobile computing device 150 related to the device's location, position, orientation, and/or motion. Such information may be processed by, for example, one or more software modules 151 (such as the rules engine 163) as described above, such that displayed image data may be updated. The mobile computing device may include a position transmitter 170 that may be used to track the position of mobile computing device 150 using, for example, RFID or Bluetooth technology. Additionally, as described above, the system may also include, in some embodiments, external sensors 124 that may also provide data related to the mobile computing device's position (including location and/or orientation). In various embodiments, the functionality provided by image storage 122 and/or server 120 may reside within mobile computing device 150.

The mobile computing device 150 may communicate and/or interface with other systems and/or devices. In one or more embodiments, the mobile computer device 150 may be connected to the computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. As shown in FIG. 1A, for example, the mobile computing device 150 may be in communication with the image storage 122, the server 120, and/or the external sensor(s) 124. Image storage 122 may be a database, data store, or other electronic or computer-readable medium storage device configured to store, for example, medical images and/or three-dimensional imaging data. Such medical images and/or three-dimensional imaging data may be processed, for example, by the server 120 and/or the mobile computing device 150. Further, the various components of the computing system 100 may be in communication with various other devices that may, for example, capture and provide images and/or other data to the mobile computing device 150. For example, one or more medical scanners may be connected, such as MRI scanners. The MRI scanner may be used to acquire MRI images from patients, and may share the acquired images with other devices on the network 190. The network 190 may also include one or more CT scanners. The CT scanners may also be used to acquire images and, like the MRI scanner, may then store those images and/or share those images with other devices via the network 190. Any other scanner or device capable of inputting or generating information that may be presented to the user as images, graphics, text or sound may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) and/or PACS workstation. The PACS System may be used for the storage, retrieval, distribution and presentation of images (such as those created and/or generated by the MRI scanner and/or CT Scanner). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS). In an embodiment, the radiology information system may be a computerized system that is used by radiology departments to store, manipulate and distribute patient radiological information.

Also attached to the network 190 may be an Electronic Medical Record (EMR) system. The EMR system may be configured to store and make accessible to a plurality of medical practitioners computerized medical records. Also attached to the network 190 may be a Laboratory Information System. In an embodiment, the Laboratory Information System may be a software system which stores information created or generated by clinical laboratories. Also attached to the network 190 may be a Digital Pathology System that may be used to digitally manage and store information related to medical pathology.

Also attached to the network 190 may be one or more Computer Aided Diagnosis Systems (CAD) systems that are generally used to perform Computer-Aided Processing (CAP) such as, for example, CAD processes. In one embodiment, the CAD systems functionality may reside in a computing device separate from computing device 150 while in another embodiment the CAD systems functionality may reside within computing device 150.

Also attached to the network 190 may be one or more Processing Systems that may be used to perform computerized advanced processing such as, for example, computations on imaging information to create new views of the information, for example, volume rendering and/or other types of processing, for example image enhancement, volume quantification, blood-flow quantification, and the like. In one embodiment, such processing functionality may reside in a computing device separate from mobile computing device 150 while in another embodiment the processing functionality may reside within mobile computing device 150.

In other embodiments, other computing devices that store, provide, acquire, and/or otherwise manipulate medical data may also be coupled to the network 190 and may be in communication with one or more of the devices illustrated in FIG. 1A, such as with the computing device 150.

Depending on the embodiment, other devices discussed herein may include some or all of the same components discussed above with reference to the mobile computing device 150 and may perform some or all of the functionality discussed herein.

ADDITIONAL EMBODIMENTS

Any process descriptions, elements, or blocks in the flow diagrams described herein and/or depicted in the attached figures should be understood as potentially representing modules, segments, or portions of code which include one or more executable instructions (as described below) for implementing specific logical functions or steps in the process. Alternate implementations are included within the scope of the embodiments described herein in which elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved.

Any of the methods and processes described above may be partially or fully embodied in, and partially or fully automated via, logic instructions, software code instructions, and/or software code modules executed by one or more general purpose processors and/or application-specific processors (also referred to as "computer devices," "computing devices," "hardware computing devices," "hardware processors," and the like). For example, the methods described herein may be performed as software instructions are executed by, and/or in response to software instruction being executed by, one or more hardware processors and/or any other suitable computing devices. The software instructions and/or other executable code may be read from a tangible computer-readable medium. A tangible computer-readable medium is a data storage device that can store data that is readable by a computer system and/or computing devices. Examples of computer-readable mediums include read-only memory (ROM), random-access memory (RAM), other volatile or non-volatile memory devices, DVD-ROMs, CD-ROMs, magnetic tape, flash drives, and/or optical data storage devices. Accordingly, a software module may reside in RAM memory, flash memory, ROM memory, EPROM memory, EEPROM memory, registers, hard disk, solid state drive, a removable disk, a CD-ROM, a DVD-ROM, and/or any other form of a tangible computer-readable storage medium.

Additionally, any of the methods and processes described above may be partially or fully embodied in, and partially or fully automated via, electronic hardware (for example, logic circuits, hardware processors, and/or the like). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A medical image computing system comprising:
   a mobile computing device including at least an electronic display;
   one or more sensors configured to provide spatial position and/or motion information associated with the mobile computing device;
   a storage device configured to store electronic software instructions; and
   one or more computer processors in communication with the electronic display, the one or more sensors, and the storage device, the one or more computer processors configured to execute the stored software instructions to cause the computing system to:
   provide a user interface on the electronic display, the user interface configured to display medical image data on the electronic display;

determine, based on the spatial position and/or motion information provided by the one or more sensors, a first spatial position of the mobile computing device in a physical space;

determine a fixed virtual spatial position of the medical image data in a virtual space corresponding to the physical space, wherein the fixed virtual spatial position of the medical image data corresponds to a fixed physical spatial position in the physical space;

receive, via the mobile computing device, a user input initially selecting the fixed virtual spatial position, wherein the fixed virtual spatial position is fixed relative to the physical space;

determine, based on the first spatial position of the mobile computing device relative to the fixed virtual spatial position of the medical image data, at least a first portion of the medical image data viewable via the electronic display;

update the user interface to include the first portion of the medical image data such that the first portion of the medical image data is displayed on the electronic display;

receive an indication from the one or more sensors of a movement of the mobile computing device from the first spatial position and relative to the fixed virtual spatial position of the medical image data initially selected via the user input;

calculate, based on the spatial position and/or motion information provided by the one or more sensors, a position difference between the first spatial position and a second spatial position of the mobile computing device;

determine, based on the position difference, the second spatial position of the mobile computing device in the physical space and relative to the fixed virtual spatial position of the medical image data initially selected via the user input;

automatically determine, based on the calculated second position difference and/or the second spatial position of the mobile computing device relative to the fixed virtual spatial position of the medical image data initially selected via the user input, at least a second portion of the medical image data viewable via the electronic display; and update the user interface to include the second portion of the medical image data such that the second portion of the medical image data is displayed on the electronic display, wherein the second portion of the medical image data is virtually positioned relative to the fixed virtual spatial position of the medical image data initially selected via the user input.

2. The computing system of claim 1, wherein the medical image data comprises an array of medical images.

3. The computing system of claim 2, wherein the array of medical images comprises a two-dimensional array of medical images, and wherein the one or more computer processors are configured to execute the stored software instructions to further cause the computing system to:

in response to the position difference indicating a lateral movement, determine the second portion of the medical image data to be at a corresponding lateral position on a plane of the two-dimensional array of medical images relative to the first portion.

4. The computing system of claim 3, wherein the first and second portions of the medical image data comprise first and second medical images of the two-dimensional array.

5. The computing system of claim 4, wherein updating the user interface to include the second portion of the medical image data includes snapping to the second medical image.

6. The computing system of claim 4, wherein updating the user interface to include the second portion of the medical image data includes smoothly panning from the first medical image to the second medical image.

7. The computing system of claim 3, wherein the one or more computer processors are configured to execute the stored software instructions to further cause the computing system to:

in response to determining that the second spatial position is to a right of the first spatial position, determine the second portion of the medical image data to be to a right of the first portion of the medical image data;

in response to determining that the second spatial position is to a left of the first spatial position, determine the second portion of the medical image data to be to a left of the first portion of the medical image data;

in response to determining that the second spatial position is above the first spatial position, determine the second portion of the medical image data to be above the first portion of the medical image data; and in response to determining that the second spatial position is below the first spatial position, determine the second portion of the medical image data to be below the first portion of the medical image data.

8. The computing system of claim 3, wherein translational and rotational motion of the mobile computing device is not used in determining the second portion of the medical image data.

9. The computing system of claim 2, wherein the one or more computer processors are configured to execute the stored software instructions to further cause the computing system to:

in response to the position difference indicating an angular movement, determine the second portion of the medical image data to be at a corresponding position on the array of medical images relative to the first portion.

10. The computing system of claim 2, wherein the array of medical images comprises a curved array of medical images.

11. The computing system of claim 1, wherein the medical image data comprises a two-dimensional array of a plurality of series of medical images, wherein the first portion of the medical image data comprises a first of the plurality of series of medical images, and wherein the one or more computer processors are configured to execute the stored software instructions to further cause the computing system to:

in response to the position difference indicating at least one of an angular movement, a lateral movement, a translational movement, or a rotational movement, determine the second portion of the medical image data to be a second of the plurality of series of medical images, the second of the plurality of series of medical images positioned at a corresponding position on the two-dimensional array relative to the first portion.

12. The computing system of claim 11, wherein each of the plurality of series of medical images is associated with an exam obtained at a different time or via a different modality.

13. The computing system of claim 11, wherein the one or more computer processors are configured to execute the stored software instructions to further cause the computing system to:

in response to an input from a user of the mobile computing device, updating the user interface to display a particular image of the second of the plurality of series of medical images.

14. The computing system of claim 13, wherein, during the input from the user, other movement of the mobile computing device that would otherwise be used to select a different of the plurality of series of medical images is ignored.

15. The computing system of claim 13, wherein the input comprises at least one of a touch input or a combination of a touch input and a movement of the mobile computing device.

16. The computing system of claim 1, wherein the medical image data comprises a plurality of two-dimensional medical images ordered one after another front to back in a virtual space, wherein the first portion comprises a first medical image of the plurality of two-dimensional medical images, and wherein the one or more computer processors are configured to execute the stored software instructions to further cause the computing system to:
in response to the position difference indicating a translational movement, determine the second portion of the medical image data to be at a corresponding second medical image of the plurality of two-dimensional medical images relative to the first medical image.

17. The computing system of claim 1, wherein:
the medical image data comprises a plurality of two-dimensional series of medical images,
each of the plurality of two-dimensional series shows a same anatomical part from differing orientations,
the first and second portions of the medical image data comprise medical images selected from the plurality of two-dimensional series of medical images,
the first portion of the medical image data comprises a first medical image from a first two-dimensional series, and
the one or more computer processors are configured to execute the stored software instructions to further cause the computing system to:
in response to the second spatial position comprising a rotation of the mobile computing device with reference to the first spatial position and relative to the fixed virtual spatial position of the medical image data initially selected via the user input, determine the second portion of the medical image data to be a second medical image from a second two-dimensional series showing the anatomical part from a corresponding rotated position.

18. The computing system of claim 1, wherein:
the medical image data comprises a plurality of two-dimensional series of medical images,
at least two of the plurality of two-dimensional series shows a same anatomical part from a same orientation,
the first and second portions of the medical image data comprise medical images selected from the plurality of two-dimensional series of medical images, and
the one or more computer processors are configured to execute the stored software instructions to further cause the computing system to:
in response to the second portion of the medical image data comprising a medical image from one of the at least two of the plurality of two-dimensional series, allowing a user of the mobile computing device to select one of the at least two of the plurality of two-dimensional series and determining the second portion of the medical image data to be a corresponding medical image from the selected on of the at least two of the plurality of two-dimensional series.

19. The computing system of claim 18, wherein the one or more computer processors are configured to execute the stored software instructions to further cause the computing system to:
notify the user of the existence of the at least two of the plurality of two-dimensional series before allowing the user to select the one of the at least two of the plurality of two-dimensional series.

20. The computing system of claim 1, wherein the medical image data comprises three-dimensional medical image data.

21. The computing system of claim 20, wherein the one or more computer processors are configured to execute the stored software instructions to further cause the computing system to:
utilize the second spatial position of the mobile computing device as a rendering parameter for rendering a view of the three-dimensional medical image data corresponding to the second spatial position.

22. The computing system of claim 20, wherein the first spatial position, the second spatial position, the position difference, the fixed virtual spatial position, and the fixed physical spatial position include at least one of location or orientation information.

23. The computing system of claim 20, wherein the first and second portions of the medical image data comprise rendered slices of the three-dimensional medical image data.

24. The computing system of claim 23, wherein the rendered slices of the three-dimensional medical image data are rendered in response to the received indication of the movement of the mobile computing device.

25. The computing system of claim 20, wherein the first and second portions of the medical image data comprise rendered volumes of the three-dimensional medical image data.

26. The computing system of claim 20, wherein the first and second portions of the medical image data comprise two-dimensional images of sections of the three-dimensional medical image data.

27. The computing system of claim 20, wherein the one or more computer processors are configured to execute the stored software instructions to further cause the computing system to:
in response to the position difference indicating a translational movement, determine the second portion of the medical image data to be at a corresponding translated position in the three-dimensional medical image data relative to the first portion.

28. The computing system of claim 20, wherein the one or more computer processors are configured to execute the stored software instructions to further cause the computing system to:
in response to the position difference indicating a rotational movement, determine the second portion of the medical image data to be at a corresponding rotated position in the three-dimensional medical image data relative to the first portion and relative to the fixed virtual spatial position of the medical image data initially selected via the user input.

29. The computing system of claim 20, wherein the one or more computer processors are configured to execute the stored software instructions to further cause the computing system to:
in response to the position difference indicating an arbitrary movement, determine the second portion of the medical image data to be at a corresponding arbitrary position in the three-dimensional medical image data relative to the first portion.

30. The computing system of claim 1, wherein the medical image data comprises at least one of a single medical image, an array of medical images, a series of medical images, two-dimensional medical image data, three-dimensional medical image data, a three-dimensional medical image, a three-dimensional volume, rendered portions of three-dimensional medical image data, or combinations thereof.

31. The computing system of claim 1, wherein the mobile computing device comprises at least one of a smartphone, a tablet, a smartwatch, or a wearable mobile computing device.

32. The computing system of claim 1, wherein the one or more sensors are housed in the mobile computing device and comprise at least one of an accelerometer, a gyroscope, or a Global Positioning System transceiver.

33. The computing system of claim 1, wherein the one or more sensors are located external to the mobile computing device and comprise at least one of a video camera or an infrared camera.

34. The computing system of claim 1, wherein the fixed virtual spatial position of the medical image data in the virtual space is determined based on user preferences.

\* \* \* \* \*